United States Patent [19]

Grieve et al.

[11] Patent Number: 5,663,042
[45] Date of Patent: Sep. 2, 1997

[54] DEVELOPING AGENTS FOR (PHOTO) THERMOGRAPHIC SYSTEMS

[75] Inventors: Duncan McL. A. Grieve, Saffron Walden, Great Britain; Justine A. Mooney, Austin, Tex.; William E. Bottomley, Harlow, Great Britain; John H. A. Stibbard, Bishops Stortford, Great Britain; Andrew W. Mott, Harlow, Great Britain; Robert J. D. Nairne, Loughton, Great Britain; David C. Bays, Harlow, Great Britain; Stephen S. C. Poon, Woodbury, Minn.; Raymond J. Kenney, Mahtomedi, Minn.; Gilbert L. Eian, Woodbury, Minn.; Takuzo Ishida; Doreen C. Lynch, both of St. Paul, Minn.; Roger A. Mader, North Lake Elmo, Minn.; Sharon M. Simpson; Kim M. Vogel, both of St. Paul, Minn.

[73] Assignee: Minnesota Mining and Manufacturing Company, St. Paul, Minn.

[21] Appl. No.: 382,899

[22] Filed: Feb. 3, 1995

[30] Foreign Application Priority Data

Mar. 11, 1994 [GB] United Kingdom .................. 9404805

[51] Int. Cl.$^6$ ........................................ G03C 1/498
[52] U.S. Cl. .................... 430/619; 430/223; 430/224; 430/225; 430/617
[58] Field of Search .......................... 430/223, 332, 430/203, 955, 351, 561, 617, 619, 225, 226, 224.1

[56] References Cited

U.S. PATENT DOCUMENTS 4,713,316  12/1987  Kubodera et al. .................. 430/351
5,316,887   5/1994  Arnost et al. .

FOREIGN PATENT DOCUMENTS 0 177 328  9/1986  European Pat. Off. .
0 385 496  5/1990  European Pat. Off. .
62-65037   3/1987  Japan .
2 100 016  12/1982  United Kingdom .
2 100 458  12/1982  United Kingdom .
2 198 139  9/1987  United Kingdom .

OTHER PUBLICATIONS

European Patent Application No. 0 149 260 A1, published on Jul. 24, 1985, relating to "Compounds for Use in Dye Diffusion Transfer Process and Photographic Elements Incorporating Them".

European Patent Application No. 0 343 717 A2, published on Nov. 29, 1989, relating to "UV Stabilizers for Organic Polymers".

European Patent Application No. 0 350 202, A3, published on Jan. 10, 1990, relating to "Photothermographic Elements".

Journal of Organic Chemistry of the USSR, Russian original vol. 21, No. 3, Part 2, Mar., 1985, pp. 565–570.

*Primary Examiner*—Thorl Chea
*Attorney, Agent, or Firm*—Gary L. Griswold; Walter N. Kirn; Mark A. Litman

[57] ABSTRACT

A thermographic element comprising in a non-aqueous binder medium a silver salt oxidizing agent in reactive association with a compound comprising a plurality of redox color releasing moieties such that oxidation of each redox color releasing moiety causes release from said compound of a thermally diffusible dye.

The compounds many of which are new incorporate two or more developer moieties into a single molecule to minimize the diffusibility of the compound. Following oxidation, either directly by the silver salt or by means of a cross-oxidizing agent, each oxidized developer moiety releases a thermally diffusible dye. The compounds are of sufficient size and molecular weight to slow or prevent diffusion in imaging systems and yet possess several active developer moieties per molecule which is advantageous over known ballasted dye releasers which comprise bulky molecules with only a single developer moiety.

29 Claims, 3 Drawing Sheets

DEVELOPING AGENTS FOR (PHOTO) THERMOGRAPHIC SYSTEMS

FIELD OF THE INVENTION

This invention relates to novel compounds which have utility as colour developers in thermographic and photothermographic systems. The invention also relates to thermographic and photothermographic elements containing colour developers.

BACKGROUND TO THE INVENTION

Photothermographic (i.e., heat developable photographic) imaging materials that are classified as "dry silver" compositions or emulsions comprise a light insensitive, reducible silver source, a light sensitive material which generates silver (i.e., a Ag° latent image) when irradiated, and a reducing agent for the reducible silver source. The light sensitive material is generally photographic silver halide, which must be in catalytic proximity to the light insensitive, reducible silver source. Catalytic proximity requires an intimate physical association of these two materials so that when silver specks or nuclei are generated by the irradiation or light exposure of the photographic silver halide, those nuclei are able to catalyze the reduction of the reducible silver source by the reducing agent. It has been long understood that silver (Ag°) is a catalyst for the reduction of silver ions and the silver-generating light sensitive silver halide catalyst progenitor may be placed into catalytic proximity with the silver source in a number of different fashions, such as partial metathesis of the reducible silver source with a halogen-containing source (e.g., U.S. Pat. No. 3,457,075), coprecipitation of silver halide and reducible silver source material (e.g., U.S. Pat. No. 3,839,049), and other methods that intimately associate the silver halide and the silver source.

The reducible silver source is a material that contains silver ions. The preferred reducible silver source comprises silver salts of long chain aliphatic carboxylic acids, usually having from 10 to 30 carbon atoms. The silver salt of behenic acid or mixtures of acids of similar molecular weight have been primarily used. Salts of other organic acids or other organic materials, such as silver imidazolates have been proposed, and U.S. Pat. No. 4,260,677 discloses the use of complexes of inorganic or organic silver salts as image source materials.

In both photographic and photothermographic emulsions, exposure of the photographic silver halide to light produces small clusters of silver atoms (Ag°). The imagewise distribution of these clusters is known in the art as a latent image. This latent image generally is not visible by ordinary means and the light sensitive article must be further processed in order to produce a visual image. The visual image is produced by the catalytic reduction of silver ions, which are in catalytic proximity to the silver halide grains bearing the latent image.

There are several imaging systems in which the thermal reduction of silver ion to silver metal by means of an oxidisable developer generates a colour image.

One conventional way of obtaining colour images from photothermographic emulsions is by the inclusion of dye forming materials into the emulsion. Upon imaging and thermal development, a compound is oxidised to form a dye and a reduced silver image is simultaneously formed in the exposed region. In this way a dye enhanced silver image can be produced, as shown for example in U.S. Pat. Nos. 3,531,286, 4,187,108, 4,426,441, and 4,460,681.

Dye-containing photothermographic systems in which the reactants and products remain in contact after imaging can result in several problems. For example, turbid and hazy colour images are often formed due to dye contamination with the reduced metallic silver image in the exposed area of the material after thermal development. Additionally, the resulting prints tend to develop colour in the non-imaged background. This "background stain" is caused by slow oxidation of dye precursors during storage.

In the case of purely thermographic media, image-wise application of heat generates the image and light-sensitive silver halide is not generally present. Those systems also suffer from the problem that the presence of a black silver image in addition to the desired colour dye image may lead to turbid or 'muddy' images.

One method of overcoming this problem is to transfer the dye image to a receptor or a receiving layer remote from the layer(s) containing silver. However, to provide good colour separation and background stability it is important to be able to transfer the dye image without transfer of other components, e.g., leuco dyes which may air-oxidise in the receptor and cause stain.

An attractive solution is to design the development chemistry such that the coloured species constituting the desired image is cleaved from a developer molecule in the redox development process in a form that is susceptible to thermal diffusion to a receiving layer remote from the layer(s) containing the silver.

The redox cleavage may be mediated directly by interaction with the silver salt or indirectly, by means of a "cross-oxidising agent". The latter is a compound capable of being oxidised by a silver salt and whose oxidised form participates in the redox reaction which results in the release of the dye.

British Patent No. 2100458 discloses the use of sulphonamidophenol and sulphonamidonaphthol dye-releasing redox compounds which release a diffusible dye on heat development. British Patent No. 2100016 discloses the use of dye-releasing couplers which, in combination with a reducing agent, release a diffusible dye on heat development. Various other dye-releasing systems have been disclosed, e.g., U.S. Pat. Nos. 4,060,420, 4,088,469, 4,499,180, 4,511,650, and 4,731,321, often involving thermal generation of a basic substance.

An example of suitable redox cleavage chemistry is the so-called "preformed dye release" disclosed in U.S. Pat. No. 4,981,775, in which a dye chromophore is linked to a developer moiety by a carbonyl group in a manner such that the dye is released upon oxidation of the developer and may be sublimed to a separate receptor sheet. In one example, the developer moiety is equipped with long alkyl chain substituents for ballasting purposes in order to promote selective sublimation of the released dye.

Another example of preformed dye release is the chemistry disclosed in U.S. Pat. No. 4,463,079, which discloses the use in non-aqueous photothermographic media compounds of formula:

in which;

R represents a reducing group capable of being oxidised by an organic silver salt and D represents an image forming dye part. In all the examples given, the bond between R and $SO_2$ forms a sulphonamide group.

Similar compounds are disclosed in U.S. Pat. No. 4,740,455 and references cited therein and European Pat. No. 385496 in the context of aqueous-coated photothermographic media. Base is normally required to effect the dye release.

Japanese Patent Application No. 62-065037 discloses heat-developing photosensitive media comprising silver halide, binder, reducing agent and a dye donative compound which is a polymer derived from a monomer of formula:

$$Q-X-SO_2\text{-Dye}$$

in which;

Q is an ethylenically unsaturated group,

X is an oxidisable group and,

Dye is the residue of an image forming dye formed by the extraction of a hydrogen atom.

Following exposure, thermal development causes release of a diffusible dye. The media disclosed are aqueous based, and do not contain silver salts other than photosensitive silver halide.

U.S. Pat. No. 4,713,316 discloses the use in photothermographic media of dye providing substances of formula:

$$(\text{Dye}-X)_q Y$$

in which;

Dye represents a dye which becomes mobile when released from the molecule of the above formula, X represents a bond or linking group, Y represents a group which releases Dye in correspondence or counter correspondence to light sensitive silver salts having a latent image distributed imagewise, and q is 1 or 2.

The media preferably comprise an organic silver salt oxidising agent in addition to light sensitive silver halide, but only aqueous based systems are disclosed, and no advantage is taught for compounds in which q is 2.

U.S. Pat. No. 4,021,240 discloses a different colour-forming chemistry in which a p-sulphonamidophenol developer is oxidised by silver ion and then couples with a "four-equivalent" colour coupler to form a precursor which releases a dye by elimination of sulphinic acid.

A further colour-forming chemistry is disclosed in European Patent No. 177328, U.S. Pat. No. 4,622,395, and U.S. Pat. No. 4,594,307 which describe acylated phenazine, phenoxazine and phenothiazine leuco dyes. Oxidation of these leuco dyes by silver ion causes release of the corresponding azine dyes via cleavage of

bond.

A problem shared by all of these prior art approaches is that of unwanted transfer of coloured or colour-generation materials in the non-image areas, causing unacceptably high Dmin's either immediately or on storage. This is a result of insufficient mobility differential between the released dye and its precursors. A related problem arises when the media comprises two or more colour-forming layers, as in a full-colour imaging element. Unwanted migration of the colour forming compounds among the various layers can occur, particularly at the coating stage, leading to crosstalk and inaccurate colour rendition.

Various attempts have been made to reduce the mobility of the colour releasing compounds including the use of bulky alkyl ballasting groups, as disclosed in U.S. Pat. No. 4,981,775, and the use of hydrophillic groups is disclosed in U.S. Pat. No. 4,463,079. However, none of the known techniques has proved to be fully effective, especially in the context of hydrophobic media, coated from non-aqueous solvents. Controlling the diffusion of colour forming or releasing compounds is relatively easy in aqueous based systems (both wet and dry developed) owing to the special properties of the binder involved, normally gelatin or similar hydrophillic colloids. These binders form stable dispersions of the essentially hydrophobic colour forming chemistry, and because of the incompatibility of the two phases, diffusion of the colour forming chemistry within the hydrophillic binder is limited. It is common practice to heighten this incompatibility by incorporating bulky hydrophobic groups in the colour forming compounds, or by attaching the colour forming compounds to hydrophobic polymer backbones, as is frequently done with colour couplers in conventional colour negative film. However, this biphasic approach is very difficult in the case of non-aqueous based media, where the binders used are essentially hydrophobic and cannot easily be made to be incompatible with the colour generating chemistry.

U.K. Patent Application No. 2198139 discloses polymeric leuco dyes for use in heat sensitive or light and pressure sensitive recording materials. The polymeric leucos become coloured on contact with electron accepting (acidic) compounds, but do not release a diffusible dye.

Likewise, Japanese Patent Application No. 50-020809 discloses compounds formed by the reaction between bis (acid chlorides) and reduced diazine, oxazine and thiazine dyes for use in heat or pressure sensitive media. There is no disclosure of diffusible dye release or imaging with silver salts.

It has now been found that substantial improvements in non-aqueous thermographic and photothermographic media are possible when two or more dye releasing moieties are linked together in a single molecule.

BRIEF SUMMARY OF THE INVENTION

Therefore according to the present invention there is provided a thermographic element comprising in a non-aqueous binder medium a silver salt oxidising agent in reactive association with at least one compound comprising a plurality of redox colour releasing moieties such that oxidation of each redox colour releasing moiety causes release from said compound of a thermally diffusible dye.

The invention also provides photothermographic systems which additionally comprise light-sensitive silver halide in catalytic association with the silver salt. Preferably, the photothermographic media comprises two or more separate layers each of which contains the above ingredients in which the silver halide in the separate layers is sensitised to different wavelengths and the dyes released by the redox colour releasing compounds in the separate layers are of different colours.

Many of the redox colour releasing compounds are themselves novel and constitute a further aspect of the invention.

DESCRIPTION OF PREFERRED EMBODIMENTS

Figure 1A:
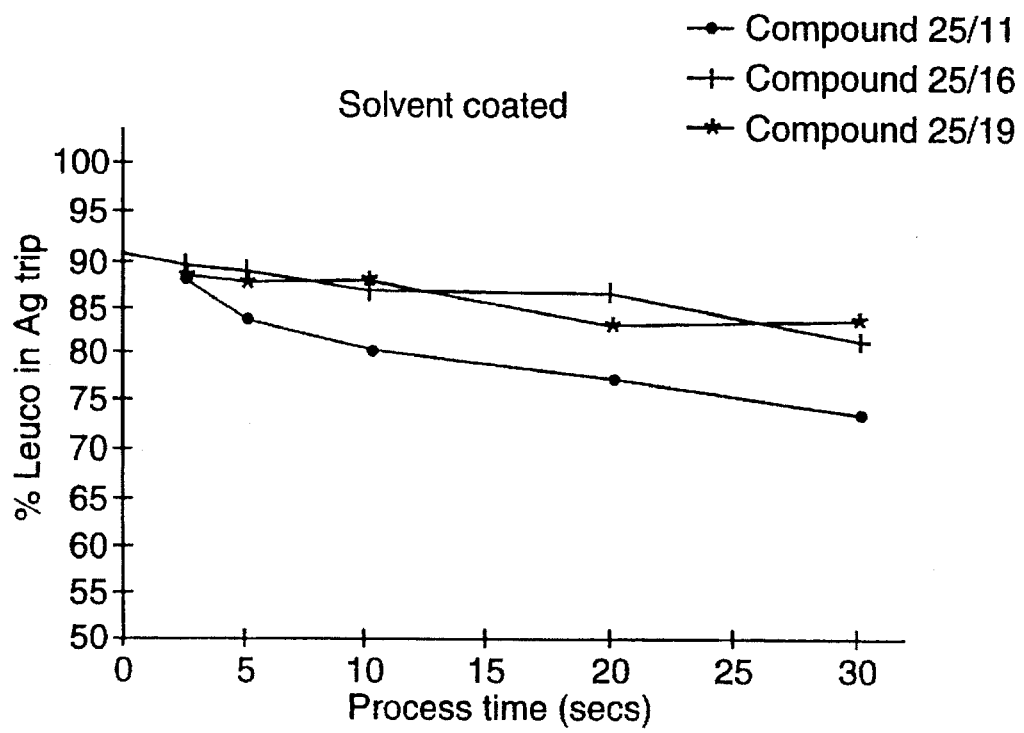
FIGS. 1a, 1b, 2, 3, 4a, and 4b show diffusion test results of samples of the imaging elements of this invention.
Figure 1B:
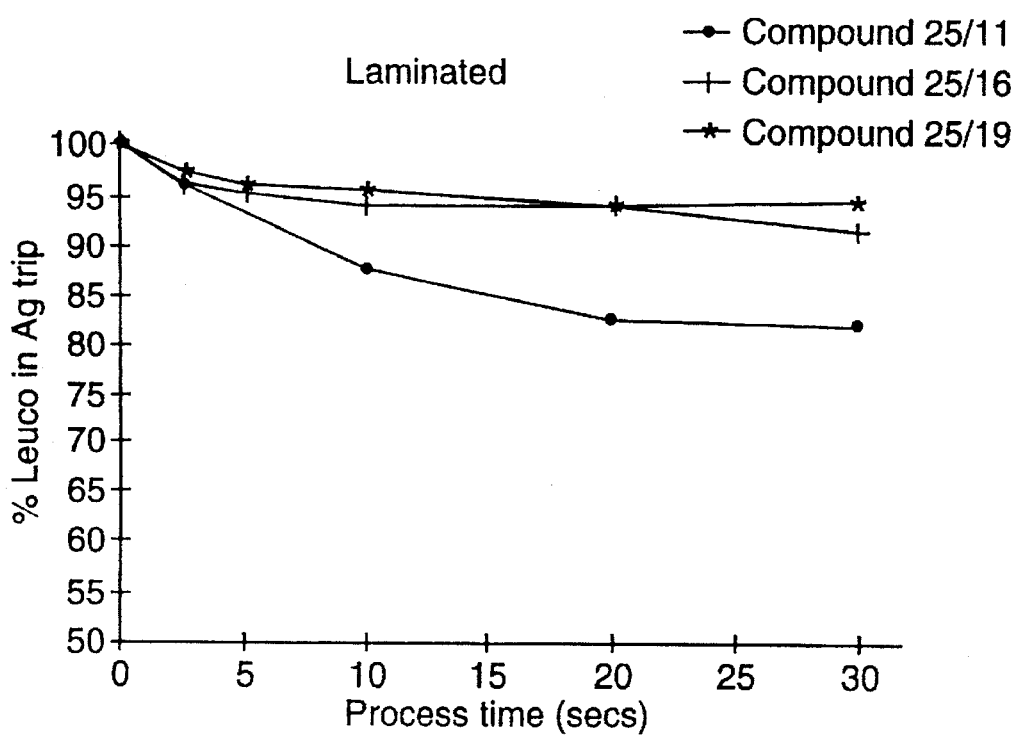
Figure 2:
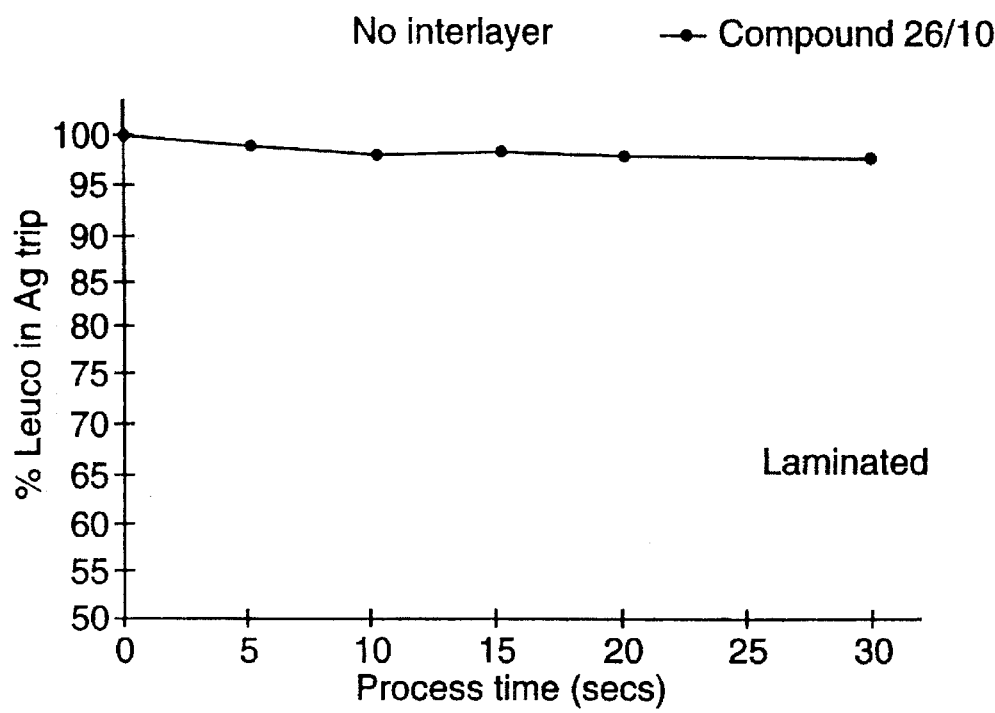
Figure 3:
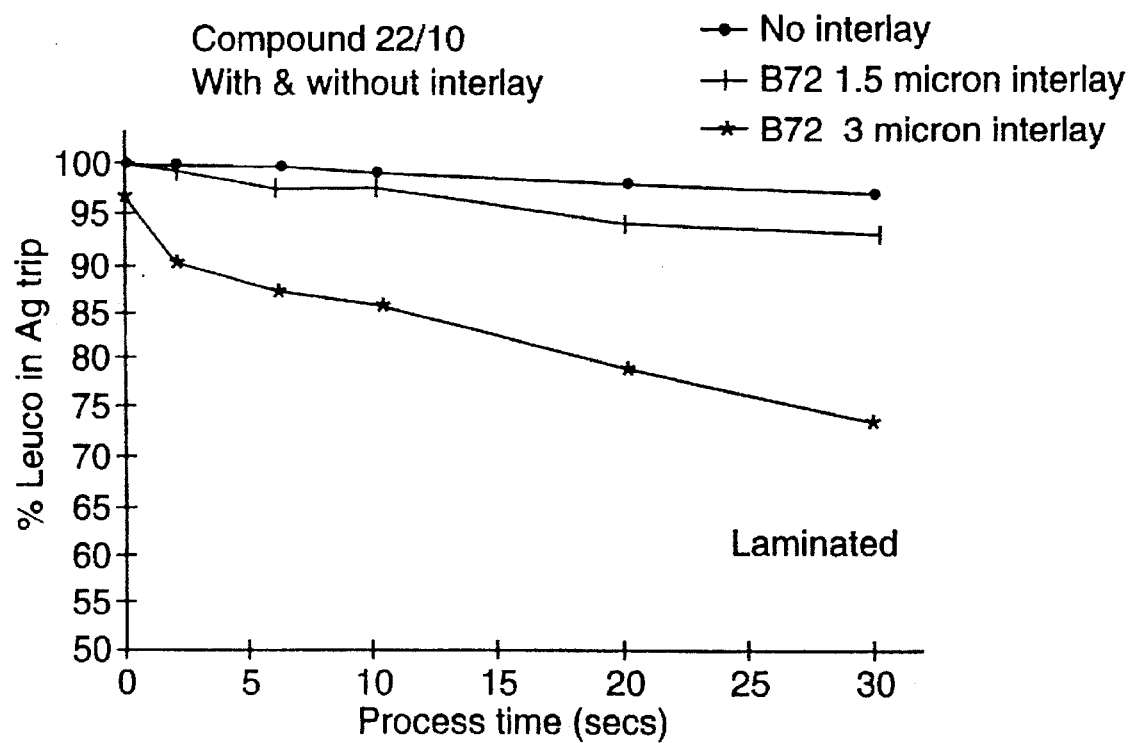
Figure 4A:
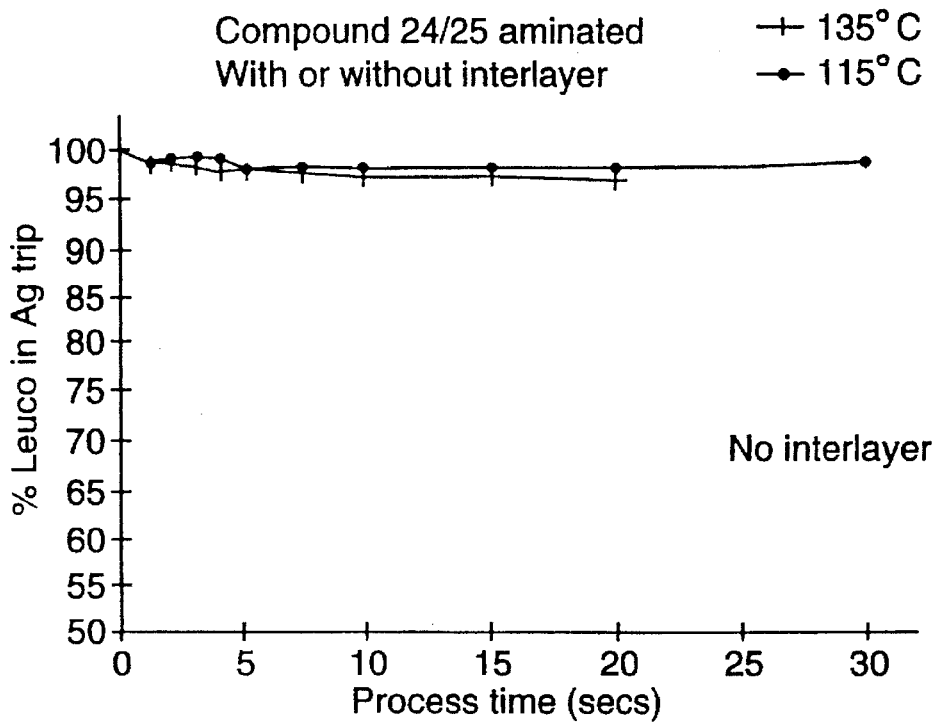
Figure 4B:
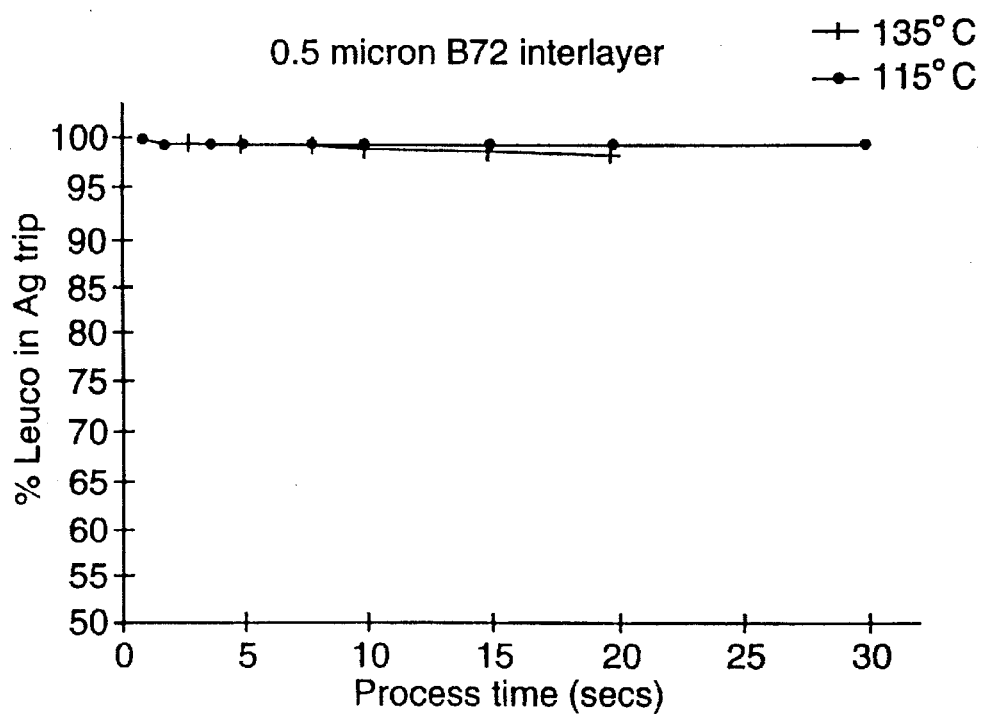

The compounds useful in the invention incorporate two or more developer moieties into a single molecule to minimise the diffusibility of the compound. Following oxidation, either directly by the silver salt or by means of a cross-oxidising agent, each oxidised developer moiety releases a thermally diffusible dye. The compounds are of sufficient size and molecular weight to slow or prevent diffusion in imaging systems and yet possess several active developer moieties per molecule which is advantageous over known ballasted dye releasers which comprise bulky molecules with only a single developer moiety.

It is a surprising feature of the invention that the redox colour releasing compounds show a very low molecular diffusivity within or between the coated layers, show a good developing action towards the silver salt oxidising agent and provide efficiently migrating dyes.

The redox colour releasing compounds may employ any of the known mechanisms for redox mediated release of a diffusible dye. These include not only mechanisms in which the dye is released directly as a result of the redox process but also those mechanisms in which release of the dye requires one or more reaction steps subsequent to the redox reaction.

For example, the compounds may incorporate preformed dye moieties attached via oxidisable groups whose oxidation causes release of the dye moiety. Many examples of this chemistry are known in the art, including those in which the oxidisable group is a sulphonamido-aryl group as described in U.S. Pat. No. 4,463,079 and U.S. Pat. No. 4,7404,55. Further examples are disclosed in U.S. Pat. No. 4,981,775 in which the oxidisable group is an acyl leuco of an azine dye.

Alternatively, the compounds may incorporate the dyes in their reduced (leuco) forms which are oxidised in the redox process, thus generating the desired chromophore, and are simultaneously cleaved from the rest of the molecule. This type of chemistry is exemplified in U.S. Pat. No. 4,594,307.

Another useful redox mediated colour releasing chemistry is the type described in U.S. Pat. No. 4,021,240. In this case, the redox colour releasing compounds comprise oxidisable groups which, in their oxidised state, may couple with a 4-equivalent colour coupler. Thermal treatment of the adduct causes release of a coloured dye. The oxidisable group in all the examples disclosed is a 2,6-dihalo-4-sulphonamidophenol.

Thus, certain compounds useful in the invention may have a structure represented by formula (I):

in which:
n is an integer of at least 2,
each A independently represents a bond or divalent linking group,
each $R^1$ independently represents a reducing group capable of being oxidised by a silver salt,
each $Y^1$ independently represents a divalent linking group capable of being oxidatively cleaved from $R^1$, and/or $D^1$,
each $D^1$ independently represents a dye moiety which forms a thermally diffusible dye on cleavage of a bond to $Y^1$, and
X represents an atom or group (e.g., monomer, oligomer or polymer) to which each A is bonded.

Further compounds useful in the invention may have a structure represented by formula (II):

in which:
X, A and n have the same meanings as in formula (I), and each $Y^2$ independently represents a divalent linking group capable of being oxidatively cleaved from A and/or $-D^2$ and each $-D^2$ independently represents a leuco dye residue capable of being oxidised by a silver salt.

A third class of compounds in accordance with the invention has a structure represented by formula (III):

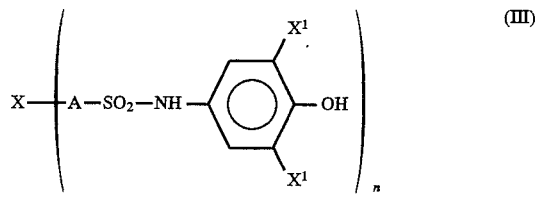

in which:
X, A and n are as defined with respect to formula (I), and each $X^1$ is independently Cl or Br.

These compounds are moieties which couple with a 4-equivalent coupler. Such redox mediated chemistry is disclosed in U.S. Pat. No. 4,021,240.

In formula (I), $-D^1$ represents any dye containing moiety which forms a thermally diffusible dye on cleavage of a bond to $Y^1$. A wide variety of dye chromophores may be incorporated in $-D^1$, such as azo, azomethine, anthraquinone, naphthaquinone, styryl, quinophthalone and phthalocyanine. Suitable examples are given in U.S. Pat. No. 4,463,079 and U.S. Pat. No. 4,981,775.

$Y^1$ represents a divalent linkage which enables the oxidative cleavage of $-D^1$. Examples of $Y^1$ include:

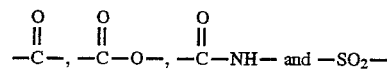

$R^1$ represents a reducing group capable of being oxidised by a silver salt, and may take a variety of forms, depending on the identity of $Y^1$. When $Y^1$ is $-SO_2-$, $R^1$ is preferably an arylamino group, typically a hydroxyarylamino group of the type disclosed in U.S. Pat. No. 4,463,079 and U.S. Pat. No. 4,740,455.

When $Y^1$ is

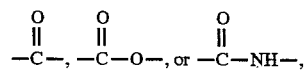

$R^1$ preferably has a structure defined by formula (IV):

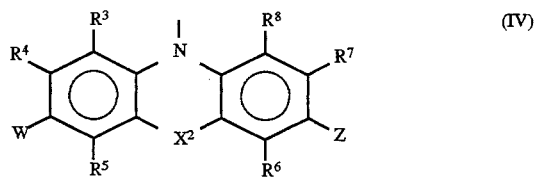

in which:
$X^2$ represents S, O, or N—R in which R represents an alkyl or aryl group,
$R^3$, $R^4$, $R^5$, $R^6$, $R^7$ and $R^8$ each independently represent hydrogen, halogen, an alkyl group, preferably having from 1 to 4 carbon atoms, or $R^3$ together with $R^4$, and $R^7$ together with $R^8$, may independently represent the atoms chosen from C, N, O, S that complete a fused ring system, preferably with 5 to 7 atoms in each ring, W and Z independently represent hydrogen, an alkyl group (preferably having from 1 to 4 carbon atoms), an alkoxy or alkythio group (preferably having from 1 to 4 carbon atoms), acyloxy, —OH, —SH, or a group represented by —NR$^9$R$^{10}$, where R$^9$ and R$^{10}$ each independently represents hydrogen, an alkyl group, an aryl group, an aralkyl group, an acyl group or an aroyl group (provided that not both of R$^9$ and R$^{10}$ are hydrogen), or where $^1$R$^9$ and R$^{10}$ together represent the necessary atoms selected from C,N,O and S to complete a 5-, 6-, or 7-membered heterocyclic ring group, or where one or both of R$^9$ and R$^{10}$, together with R$^4$, R$^5$, R$^6$ or R$^7$, represents the necessary atoms selected from C,N,O and S to complete a 5- or 6-membered heterocyclic ring group fused to the phenyl ring on which the —NR$^9$R$^{10}$ group is attached;

with the proviso that one of W, X$^2$, Z and R$^3$ to R$^8$ has an unused valency to enable bonding to A.

Preferably at least one of W and Z represents —NR$^9$R$^{10}$. Groups of this type are disclosed in U.S. Pat. No. 4,981,775.

In formula (II), —D$^2$ is the residue of a leuco dye which is oxidisable to the corresponding dye by the silver salt. The resulting dye is thermally diffusible. D$^2$ may be derived from a variety of leuco dyes, including (but not limited to) chromogenic leuco dyes of the type disclosed in EP 053308, bisphenol and bisnaphthol leuco dyes, phenolic leuco dyes, indoaniline leuco dyes, imidazole leuco dyes, azine, oxazine, diazine and thiazine leuco dyes, and aldazine and ketazine leuco dyes. Suitable leuco dyes are disclosed in U.S. Pat. No. 4,460,681, U.S. Pat. No. 4,594,307, U.S. Pat. No. 4,587,211 and U.S. Pat. No. 4,795,697. Preferably —D$^2$ is derived from a diazine, oxazine or thiazine leuco dye, and has a structure represented by formula (IV), wherein W, Z, X$^2$ and R$^3$ to R$^8$ have the same definition as before, with the exception that none of W, X$^2$, Z and R$^3$ to R$^8$ has an unused valency.

Y$^2$ represents a divalent linkage enabling the oxidative cleavage of the dye corresponding to D$^2$. Examples of Y$^2$ include:

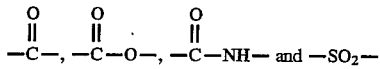

When D$^2$ is represented by formula (IV), Y$^2$ is preferably

In formulae (I) to (III), A represents a bond or a divalent linking group which joins the redox colour releasing moiety to a central core X. A may be a bond or any concatenation of atoms and rings, normally with constituent atoms selected from C, N, O, S, Si and P. There may be several different identities of A within a single molecule. The structures represented by A preferably incorporate a chain with a high degree of flexibility, such as a hydrocarbon chain of at least 6 carbon atoms, a polyether chain, a polysiloxane chain etc.

In formulae (I) to (III), X represents a central core to which 2 or more redox colour releasing moieties are attached by the groups or bonds represented by A, and n represents the number of redox colour releasing moieties attached to each X. n is an integer of 2 or more, and so the invention encompasses dimeric, trimeric, tetrameric etc. species, up to and including high molecular weight polymeric species comprising a polymeric backbone with a plurality of redox colour releasing groups pendant thereto. There is no particular upper limit for n, although values of 2, 3, 4, 5, 6, 7, 8 are common and values greater than about 100 are uncommon. X may be any atom or group with a valency of two or more, such as a carbon atom, an oxygen atom, a sulphur atom, a phosphorus atom, an aliphatic group, a ring group, fused ring group, or a polymer backbone.

Compounds of formulae (I) to (III) in which X represents a ring group are believed to be novel, and form a further aspect of the invention. Aromatic, non-aromatic homocyclic and heterocyclic rings are included, preferably with atoms selected from C, N, O, S, Si and P. Examples of preferred rings are phenyl and cyclotetrasiloxane.

Compounds of formulae (II) and (III) in which n is greater than 2 e.g. 3 to 100, are also believed to be novel, and form a further aspect of the invention. Suitable backbones are those prepared by any of the conventional polymerisation techniques, namely vinyl addition polymerisation, step growth (condensation) polymerisation and ring opening polymerisation. The polymers may be prepared by polymerisation of suitable monomers which incorporate the redox colour releasing moieties (in which case copolymerisation with "inert" comonomers is possible), or alternatively a polymer may be prepared with pendant reactive groups by means of which redox colour releasing moieties are attached to the preformed chain by a suitable linking reaction. Examples of preferred polymeric backbones include polyacrylates, polymethacrylates, polystyrenes, polyurethanes polysiloxanes, polyazlactones, polyethers and polyesters.

There are two basic strategies for the synthesis of compounds of formulae (I) to (III). In the first route, the core group X is equipped with the appropriate linking groups A, followed by attachment of redox colour releasing moieties to the ends of the A groups. In the second route, redox colour releasing moieties are synthesised to contain appropriate A groups, followed by coupling of two or more of the A groups to a suitable X group.

The invention will be illustrated with particular reference to compounds of formula (II) in which D$^2$ has the formula:

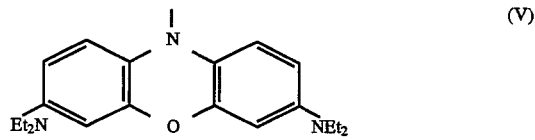

(V)

also denoted herein as "BB3" in recognition of its derivation from the leuco form of Basic Blue 3, which is a readily available commercial material. It will be understood that the principles illustrated apply equally well to all compounds of formulae (I) to (III).

Examples of dimeric compounds in accordance with the invention are shown in TABLE 1.

TABLE 1
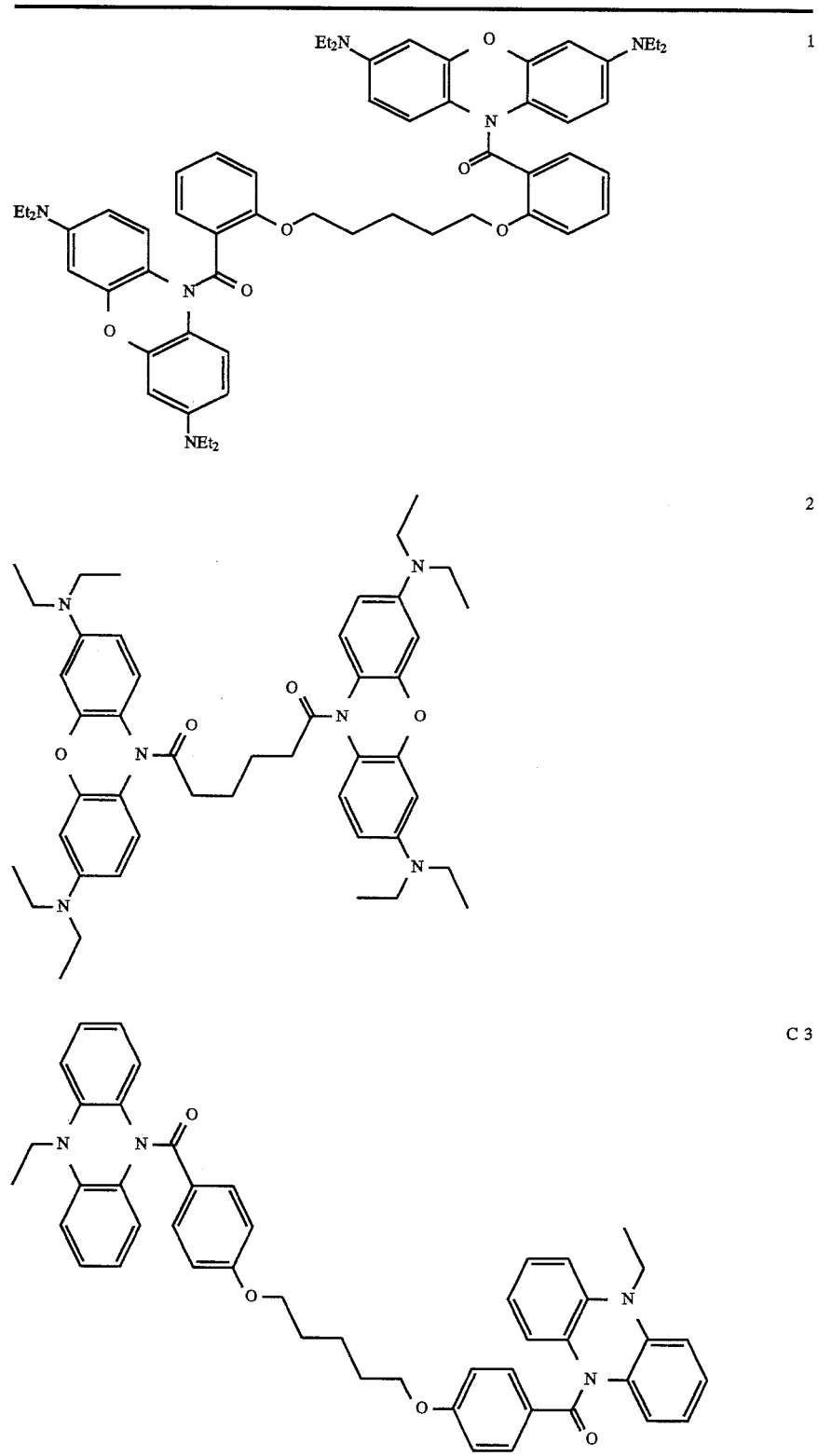

TABLE 1-continued
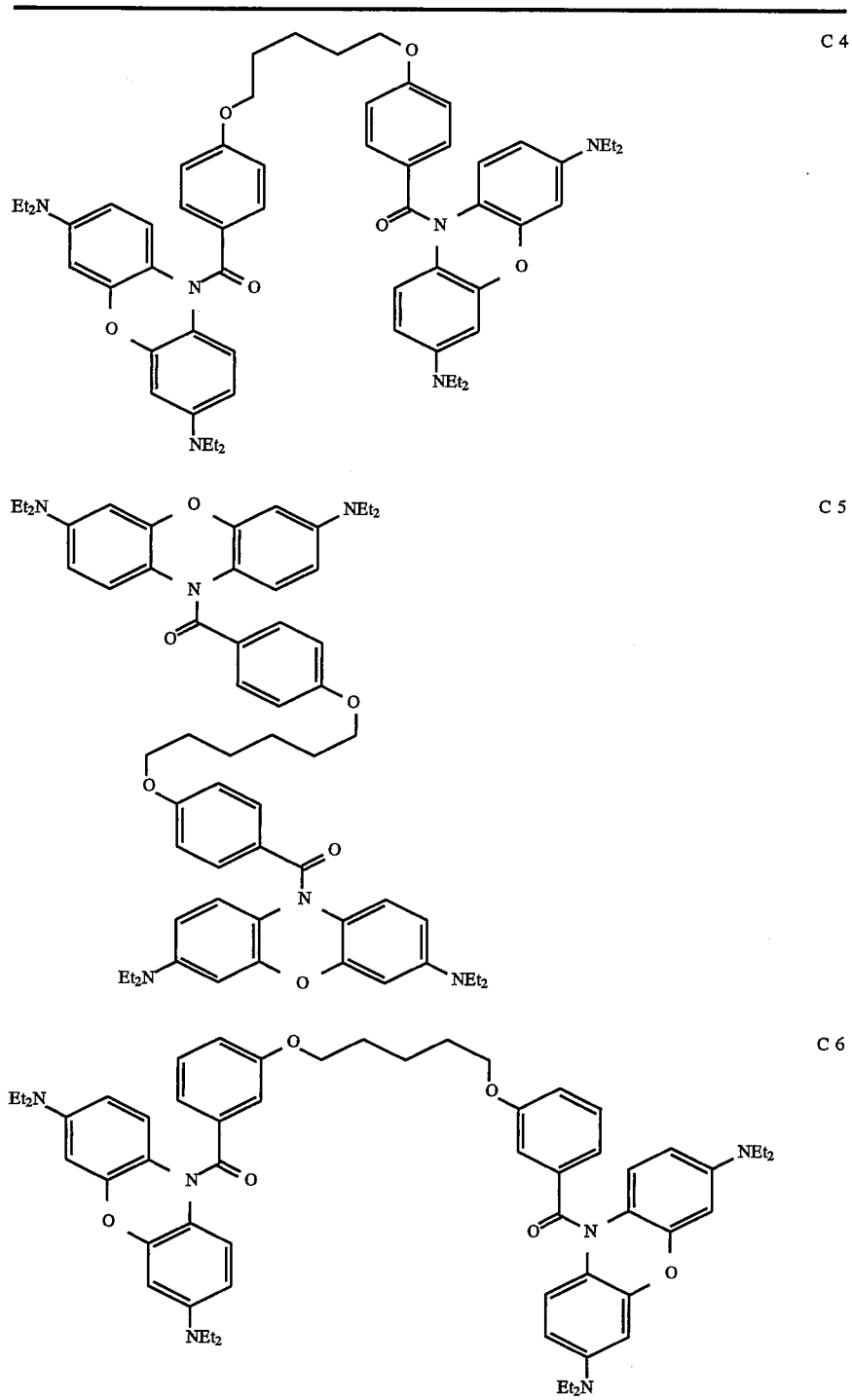

TABLE 1-continued
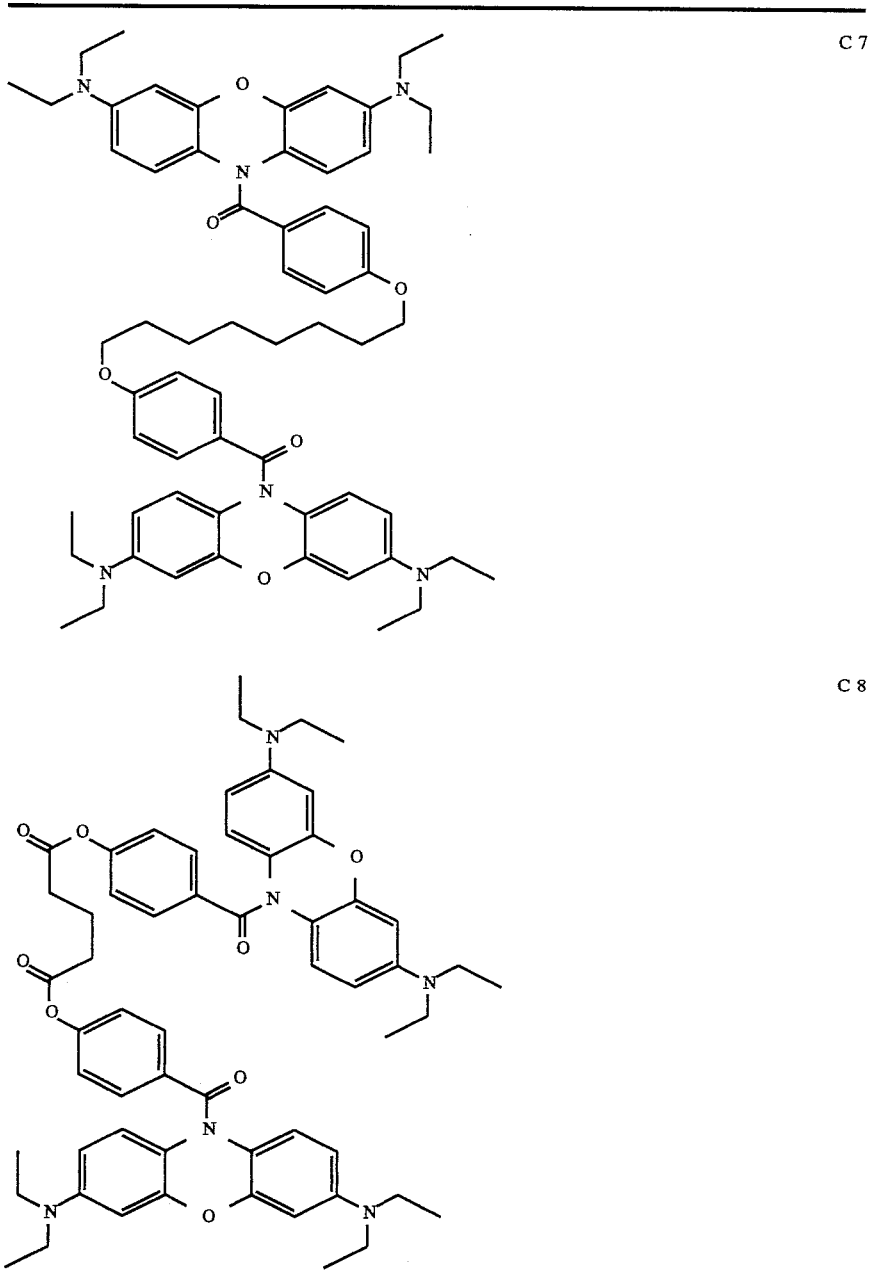

TABLE 1-continued

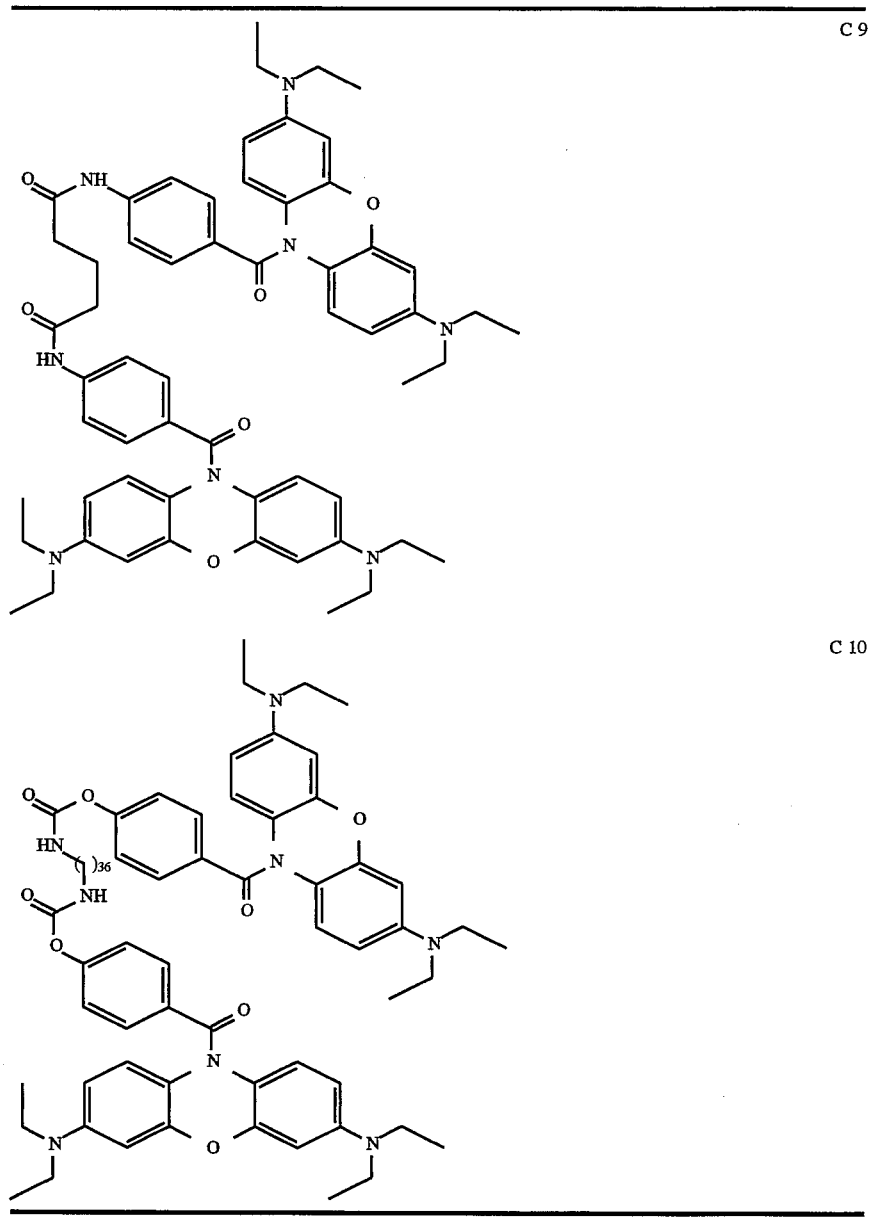

Tetrameric compounds in accordance with the invention may be prepared, for example, from 1,3,5,7-tetramethylcyclotetrasiloxane. The latter is a commercially available compound which can be readily functionalised with omega-functional terminal alkenes by a hydrosilylation reaction. Choice of a suitable omega-haloalkene gives a tetrakis(alkyl halide) which may be reacted with suitably functionalised redox colour releasing chemistry, for example, the phenolic portion of a p-hydroxybenzoylated leuco dye.

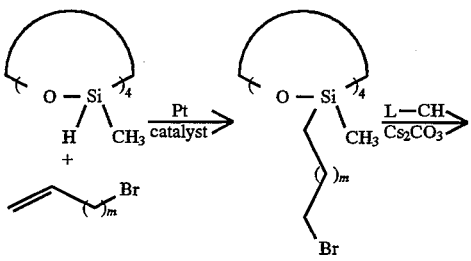

17
-continued
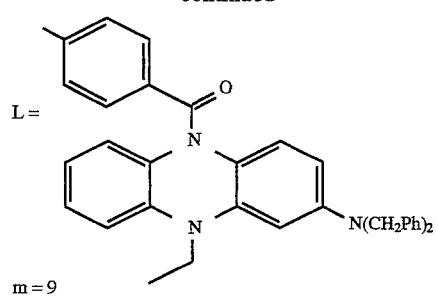
m = 9
Compound No. 12
For example,
L =
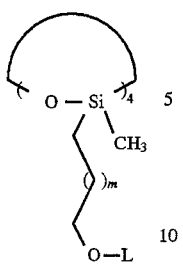
m = 9
Compound No. 11
18
-continued
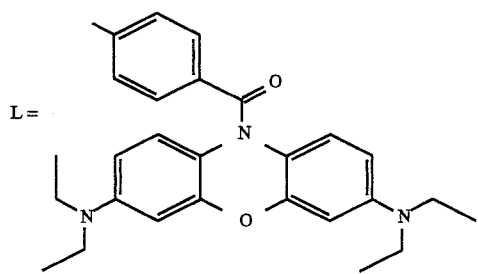
It is readily possible to prepare star compounds having 3 or 6 redox colour releasing moieties linked to a single phenyl ring.
The trimeric compounds may be prepared by the following reaction scheme:
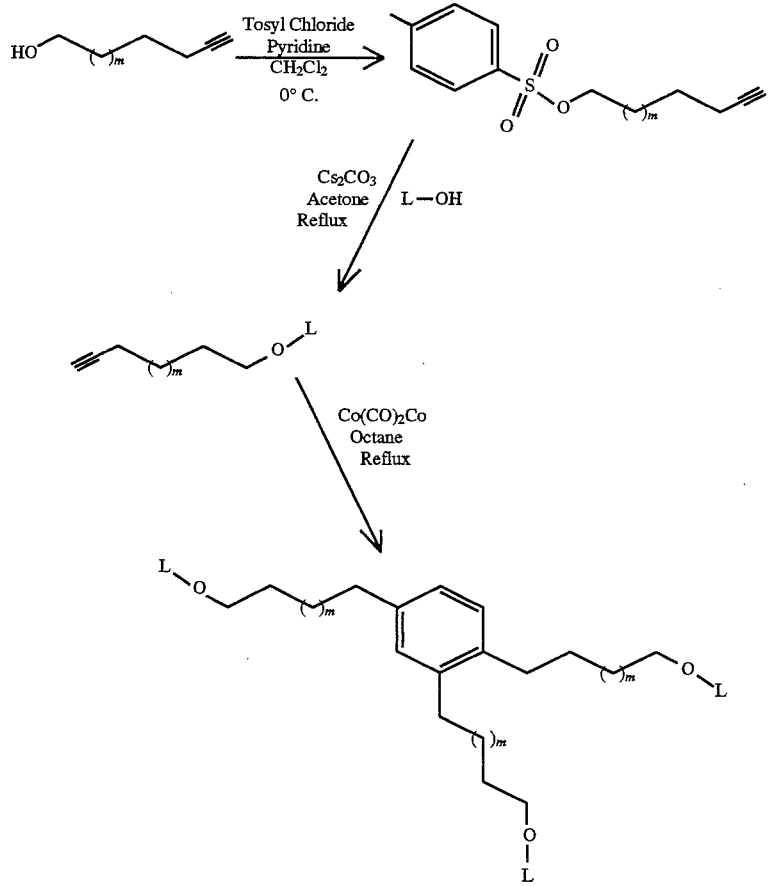

where L—OH is a hydroxy functional redox colour releasing compound, e.g. p-hydroxybenzoyl-BB3, used in preparing Compound No. 11 above.

The following trimeric compounds have been prepared by this route:

Compound No. 13 L=benzoyl-BB3, m=1, mw=1577
Compound No. 14 L=benzoyl-BB3, m=6, mw=1787.

Hexamers may be prepared by the following reaction scheme.

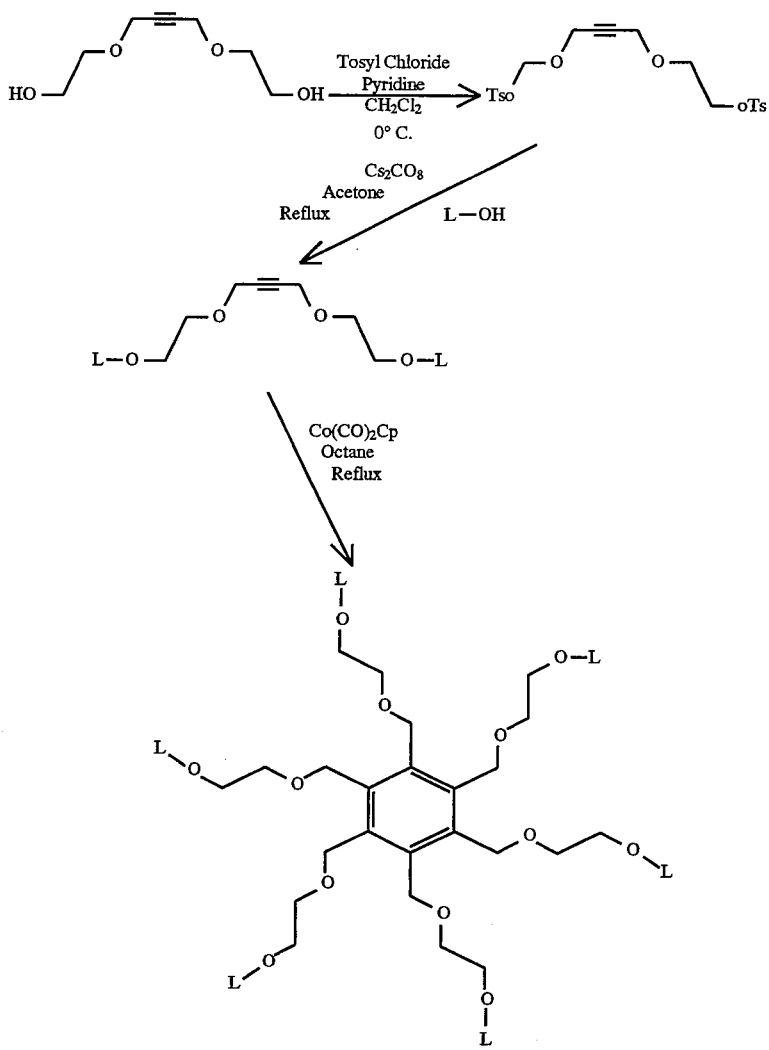

where L—OH is a hydroxy functional redox colour releasing compound, e.g. p-hydroxybenzoyl-BB3, used in preparing Compound No. 11 above.

The following hexameric compound has been prepared: Compound No. 15: L=benzoyl-BB3.

Alternative routes to polyfunctional redox colour releasing compounds include the reaction of polyfunctional isocyanates with hydroxy- or amino-functional redox colour releasing compounds, as illustrated in the following scheme:

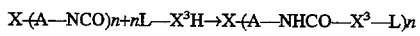

where n, X and A have the same meanings as before, $X^3$ represents O or NH, and L represents a redox colour releasing moiety.

Suitable polyfunctional isocyanates are available commercially. For example, Desmodur N3300 and Desmodur N100 are available from Miles Inc., and have the above formula in which n is 3, A is —$(CH_2)_6$—, and X is, respectively:

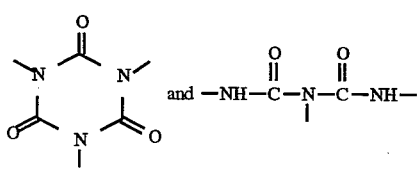

Other star molecules may be prepared by synthesising a functionalised star molecule and thereafter reacting with a redox colour releasing moiety. For example, reaction of pentaerythritol with a long-chain difunctional compound such as 10-undecenoyl chloride generates a functionalised 4-armed star molecule in good yield, which may be conveniently purified by flash chromatography. The tetraolefin can be converted into the corresponding tetraacid by oxidative cleavage using a modification of Sharpless' procedure (J. Org. Chem., 1981, 46, 3936). Reaction of the tetraacid with a suitably functionalised redox colour releasing moiety then affords the target star-ballasted dye releaser.

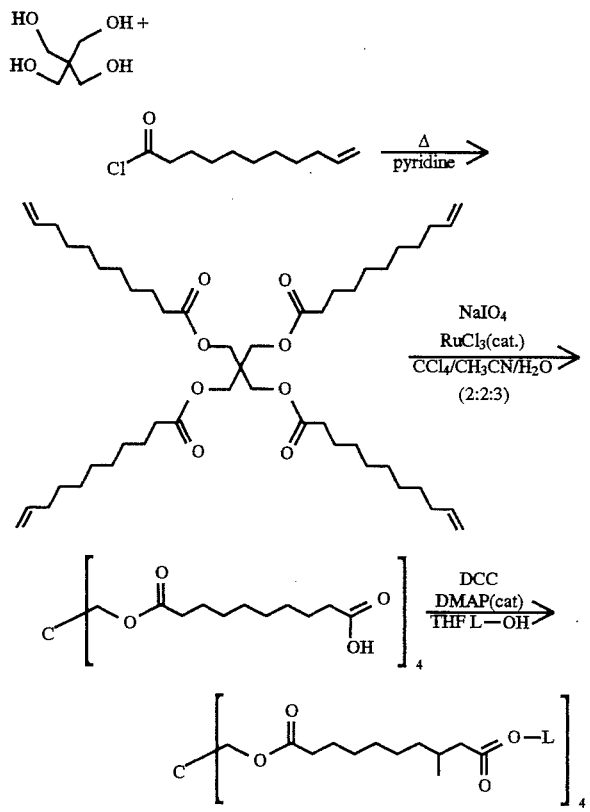

where L—OH has the same meaning as before.

Other centers for the star may be formed by suitable selection of starting materials. For example, a functionalised 6-armed star molecule may be obtained by using sugar inositol in place of pentaerythritol.

A wide range of polymers may be prepared having pendant redox colour releasing units.

Polymeric leucos, for example, may be prepared with the backbones such as poly(meth)acrylates, polystyrenes, polysiloxanes and polyurethanes. These backbones include examples of both addition and condensation type polymers; polymers with differing solubilities; polymers prepared both by polymerisation of the leuco monomer and by grafting the leuco onto an existing polymer.

During the oxidation process of azine leuco dyes in photothermographic systems the protecting group, usually an N-acyl moiety, is cleaved. This provides the opportunity for ballasting a leuco dye by adding physical bulk to the protecting group without affecting the size of the dye formed, and therefore its mobility. In the case of high Mw polymers it is preferable to attach the bulky leuco moiety to the backbone via a flexible spacer to allow mobility of the side chain. It appears a flexible spacer group of at least six atoms is desirable.

Polymers with varying molecular weight and glass transition temperature (Tg) may be prepared. Tg may be controlled by copolymerisation in the case of poly(meth) acrylates and polystyrenes, and by selection of an appropriate diisocyanate or diol the case of polyurethanes. The Tg should be less than the development temperature of the photothermographic media, e.g. less an 100° C. For addition polymers, chain transfer agents may be employed to control molecular weight.

Molecular weight (Mw) effects both the reactivity and the diffusion characteristics of the polymeric leuco. Results suggest an optimum value of around 15,000 in the case of vinyl addition polymers when the conditions of Tg are also satisfied.

(Meth)acrylate leuco monomers may be prepared by the reaction of hydroxy- or amino-functional leucos, for example, omega-hydroxyalkoxybenzoyl leucos, with (meth) acryloyl chloride. These may be homopolymerised or copolymerised to yield the corresponding poly(meth)acrylate leucos. Reactivity was found to be enhanced in a copolymer compared to the equivalent homopolymer.

For example:

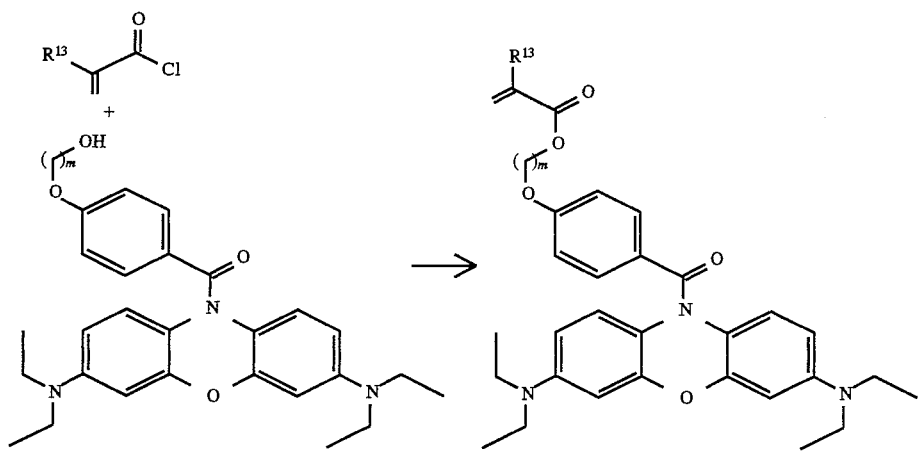

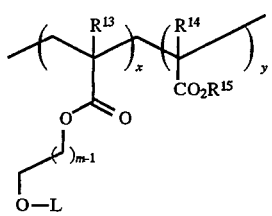

in which:

$R^{13}$, $R^{14}$ are independently selected from H, alkyl or halogen, and $R^{15}$ is H, alkyl or aryl.

The following polymers have been prepared. x and y represent the weight percentage of each monomer.

| Compound No. | m | $R^{13}$ | $R^{14}$ | $R^{15}$ | x | y |
|---|---|---|---|---|---|---|
| 16 | homopolymer | 7 | H | — | — | 100 | 0 |
| 17 | copolymer | 7 | H | H | methyl | 33 | 67 |
| 18 | copolymer | 7 | methyl | methyl | butyl | 33 | 67 |
| 19 | copolymer | 7 | methyl | methyl | ethyl | 33 | 67 |
| 20 | copolymer | 7 | methyl | methyl | methyl | 33 | 67 |
| 21 | copolymer | 10 | methyl | methyl | butyl | 33 | 67 |
| 22 | copolymer | 10 | methyl | methyl | butyl | 50 | 50 |
| 23 | copolymer | 10 | methyl | methyl | ethyl | 33 | 67 |

Polystyrenes were prepared as shown below. Co-polymerisation of the styrene functional monomeric leuco with acrylate monomers resulted in block copolymers, as evidenced by two glass transition temperatures for some copolymers. However, this block character was not seen in copolymers of the styrene functional leuco monomer and methacrylate monomers. No attempt was made to determine the reactivity ratios of the various monomeric leucos used in this work.

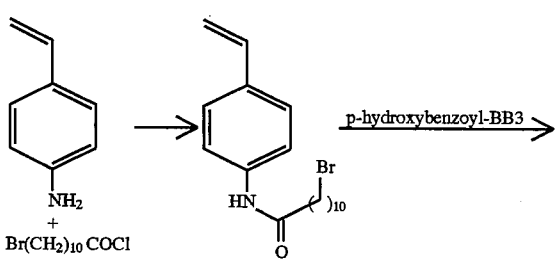

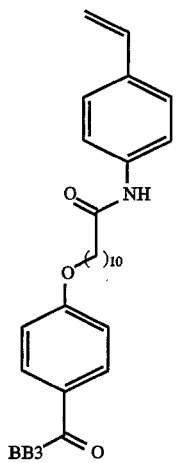

The following polymers were prepared:

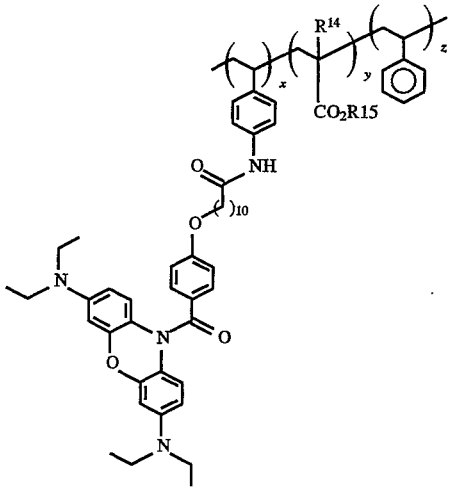

| Compound No. | $R^{14}$ | $R^{15}$ | x | y | z |
|---|---|---|---|---|---|
| 24 | H | methyl | 33 | 67 | 0 |
| 25 | methyl | butyl | 50 | 50 | 0 |
| 26 | — | — | 33 | 0 | 67 |

Polyurethane leucos are an example of condensation-type polymers. A slight excess of diisocyanate was employed to overcome the effect of side reactions. The general synthetic scheme is shown below. An alternative route would have been to first prepare the leuco diol and then prepare the polyurethane leuco by polymerisation with a diisocyanate moiety.

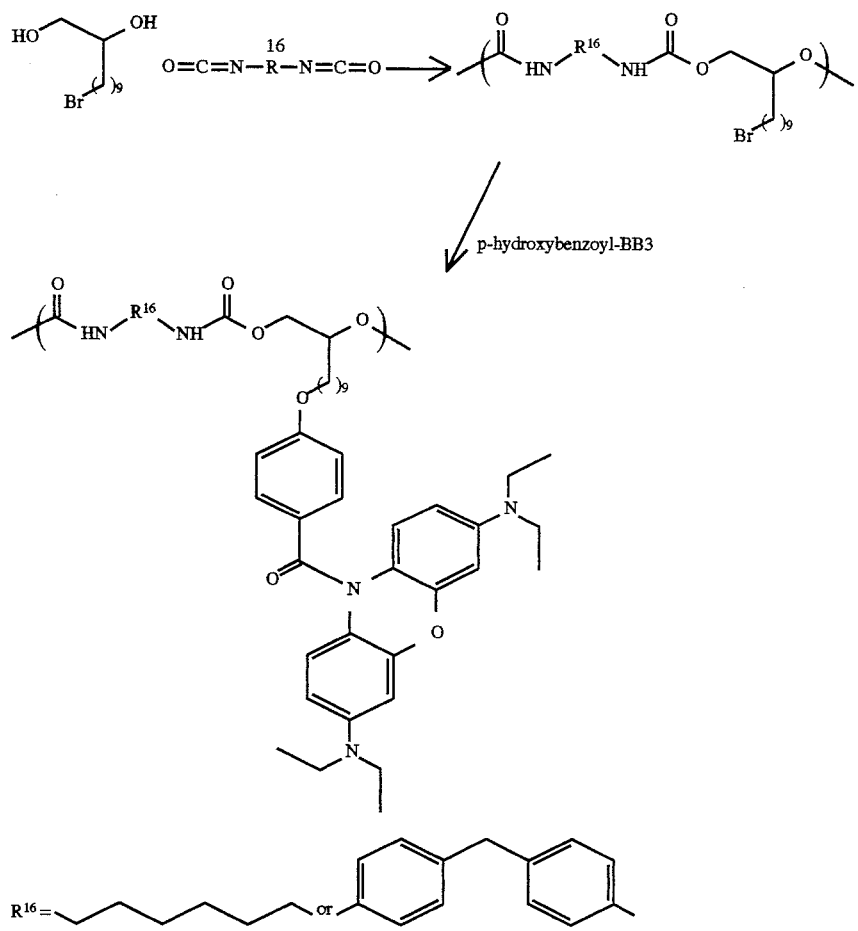
The following polymers were prepared:
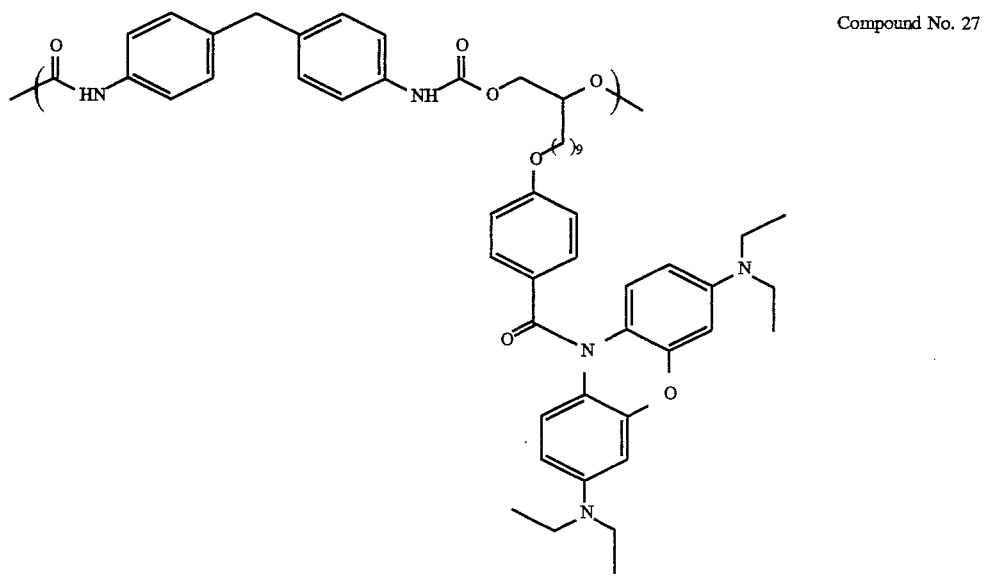
Compound No. 27

Compound No. 28

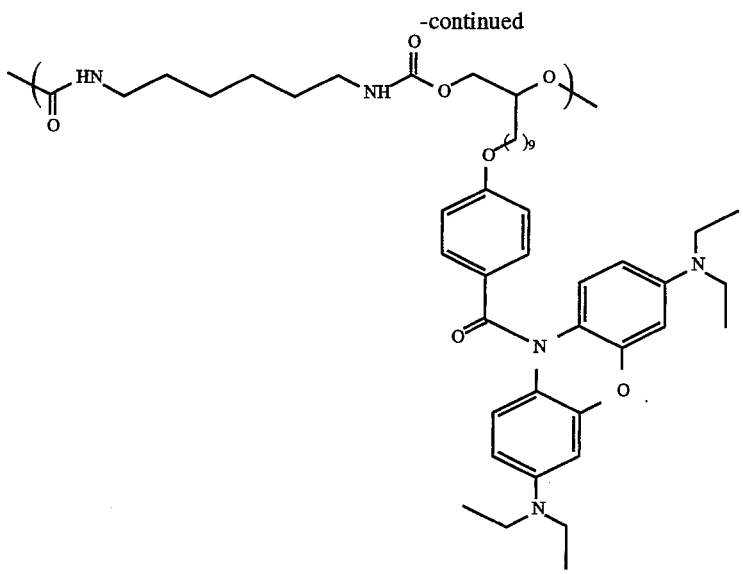

Polysiloxane leucos, like the polyurethane leucos, were prepared by grafting the leuco moiety onto an existing polymer backbone, rather than by polymerisation of a leuco monomer. The polysiloxane leuco examples were prepared using a commercially available polysiloxane. A platinum catalyst was employed to effect the attachment of a flexible side chain to the siloxane backbone, to which the leuco is then attached as shown below:

| Compound No. | $m^1$ | $X^3$ | $R^{17}$ | x | y | z | Mw | Mw/Mn |
|---|---|---|---|---|---|---|---|---|
| 29 | 11 | Br | $C_4H_9$ | 27 | 6 | 67 | 31800 | 1.71 |
| 30 | 4 | Br | $C_4H_9$ | 14 | 4 | 82 | 10400 | 1.96 |
| 31 | 10 | tosylate | $C_4H_9$ | 36 | 8 | 56 | 28600 | 1.54 |

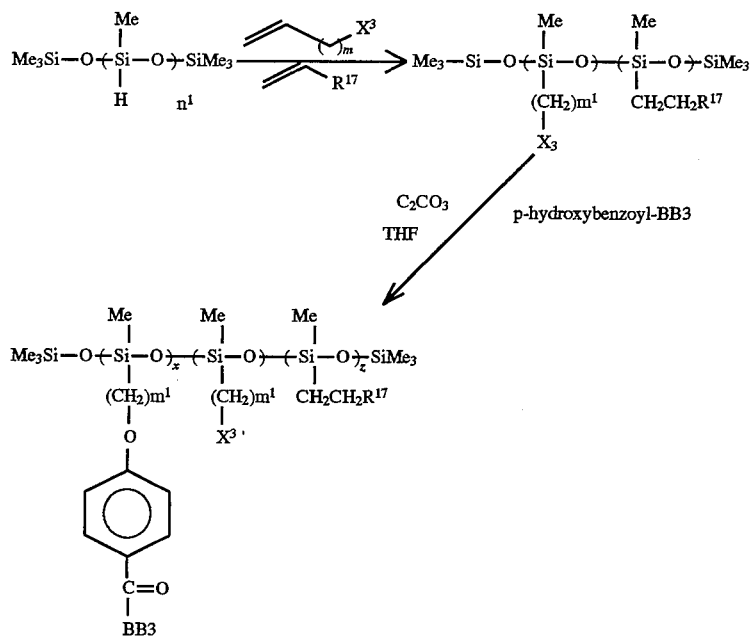

where
 $n^1$ and m are integers:
 $m^1 = m+2$,
 $R^{17}$ is alkyl group or aryl group,
 $X^3$ is a leaving group, e.g. Br, Cl or tosylate,
 x, y and z are the percentages by weight of the repeat units.

Compounds 29 to 34 in the following Table were prepared by this method:

-continued

| Compound No. | $m^1$ | $X^3$ | $R^{17}$ | x | y | z | Mw | Mw/Mn |
|---|---|---|---|---|---|---|---|---|
| 32 | 10 | Br | $C_4H_5$ | 36 | 7 | 57 | 28900 | 1.56 |
| 33 | 11 | Br | $C_6H_5$ | 35 | 10 | 55 | 18400 | 1.21 |
| 34 | 19 | Br | $C_4H_9$ | 19 | 3 | 78 | 18400 | 2.22 |

A further class of polymers which have been prepared are of the general formula:

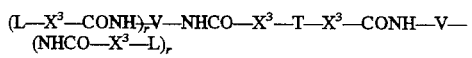

in which;

L represents a redox colour releasing moiety, each r independently represents an integer of 1 or more, each V independently represents an organic group of valency r+1, $X^1$ represents O or NH, and T represents a divalent organic group.

Such compounds may be synthesised by methods analogous to those disclosed in U.S. patent application Ser. No. 07/981,073. A polyfunctional isocyanate or mixture of polyfunctional isocyanates, of formula V—(—NCO)$_{r+1}$ is reacted with a dinucleophile of formula HX$^3$—T—X$^3$H (i.e. a diamine or a diol), with a molar ratio of polyfunctional isocyanate(s) to dinucleophile of about 2:1. This gives a chain extended polyfunctional isocyanate of formula (OCN—)$_r$V—NHCO—X$^3$—T—CONH—V—(NCO)$_r$ which may be reacted with at least 2r molar equivalents of a hydroxy- or amino-functional redox colour releasing compound to give the desired product.

The dinucleophile is advantageously a polymeric diol, such as poly(ethylene glycol), poly(tetramethylene glycol), poly(caprolactonediol) etc., or an amine terminated polymer. Suitable polyfunctional isocyanates include commercially available materials such as Desmodur N3300 and Desmodur N100, as described above.

Specific compounds of this class include those of the formula:

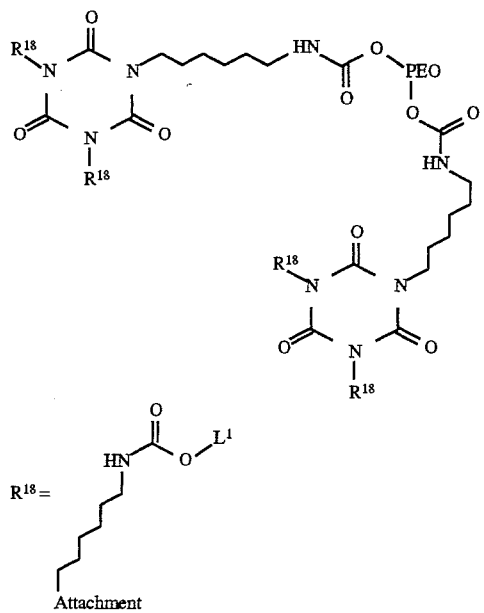

PEO=poly(ethylene oxide)
L$^1$=redox colour releasing moiety as indicated below

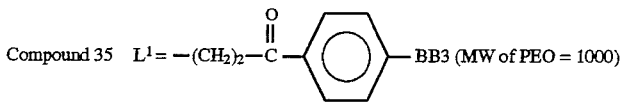

Compound 35  L$^1$= —(CH$_2$)$_2$—C(=O)—⟨phenyl⟩—BB3 (MW of PEO = 1000)

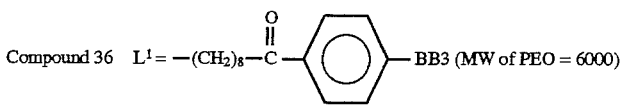

Compound 36  L$^1$= —(CH$_2$)$_8$—C(=O)—⟨phenyl⟩—BB3 (MW of PEO = 6000)

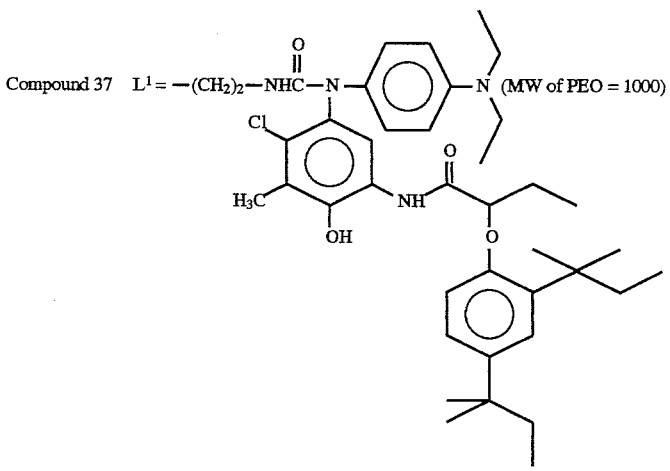

Compound 37  L$^1$= —(CH$_2$)$_2$—NHC(=O)—N... (MW of PEO = 1000)

These compounds combine low Tg (e.g. less than 0° C.) with moderately high molecular weight, and show a good balance of development activity and diffusibility.

The photothermographic dry silver emulsions of this invention may be constructed of one or more layers on a substrate. Single layer constructions must contain the silver source material (i.e. the silver salt oxidising agent), the silver halide, the redox colour releasing compound and binder as well as optional additional materials such as toners, coating aids, and other adjuvants. Two-layer constructions must contain the silver source and silver halide in one emulsion layer (usually the layer adjacent to the substrate) and some of the other ingredients in the second layer or both layers, although two layer constructions comprising a single emulsion layer containing all the ingredients and a protective topcoat are envisioned. Multicolour photothermographic dry silver constructions may contain sets of these bilayers for each colour, or they may contain all ingredients within a single layer as described in U.S. Pat. No. 4,708,928. In the case of multilayer multicolour photothermographic articles the various emulsion layers are generally maintained distinct from each other by the use of functional or non-functional barrier layers between the various photosensitive layers as described in U.S. Pat. No. 4,460,681.

Individual colour layer(s) may contain mixtures of the colour releasing compounds of the invention or the individual compounds may contain different dye groups of similar colour but different hue so as to balance colours as needed.

While not necessary for practice of the present invention, it may be advantageous to add mercury (II) salts to the emulsion layer(s) as an antifoggant. Preferred mercury (II) salts for this purpose are mercuric acetate and mercuric bromide.

The light sensitive silver halide used in the present invention may typically be employed in a range of 0.75 to 25 mol percent and, preferably, from 2 to 20 mol percent of organic silver salt, and is preferably a silver halide.

The silver halide may be any photosensitive silver halide such as silver bromide, silver iodide, silver chloride, silver bromoiodide, silver chlorobromoiodide, silver chlorobromide, etc. The silver halide may be in any form which is photosensitive including, but not limited to cubic, orthorhombic, tabular, tetrahedral, etc., and may have epitaxial growth of crystals thereon.

The silver halide used in the present invention may be employed without modification. However, it may be chemically sensitized with a chemical sensitizing agent such as a compound containing sulfur, selenium or tellurium etc., or a compound containing gold, platinum, palladium, rhodium or iridium, etc., a reducing agent such as a tin halide, etc., or a combination thereof. The details of these procedures are described in T. N. James "The Theory of the Photographic Process", Fourth Edition, Chapter 5, pages 149 to 169.

The silver halide may be added to the emulsion layer in any fashion which places it in catalytic proximity to the silver source. Silver halide and the organic silver salt which are separately formed or "preformed" in a binder can be mixed prior to use to prepare a coating solution, but it is also effective to blend both of them in a ball mill for a long period of time. Further, it is effective to use a process which comprises adding a halogen-containing compound in the organic silver salt prepared to partially convert the silver of the organic silver salt to silver halide.

Methods of preparing these silver halide and organic silver salts and manners of blending them are known in the art and described in *Research Disclosure*, June 1978, item 17029, and U.S. Pat. No. 3,700,458.

The organic silver salt may be any organic material which contains a reducible source of silver ions. Silver salts of organic acids, particularly long chain (10 to 30 preferably 15 to 28 carbon atoms) fatty carboxylic acids are preferred. Complexes of organic or inorganic silver salts wherein the ligand has a gross stability constant between 4.0 and 10.0 are also desirable. The silver source material generally constitutes from about 20 to 70 percent by weight of the imaging layer, preferably 30 to 55 percent.

The organic silver salt which can be used in the present invention is a silver salt which is comparatively stable to light, but forms a silver image when heated to 80° C. or higher in the presence of an exposed photocatalyst (such as photographic silver halide) and a reducing agent.

Preferred organic silver salts include silver salts of organic compounds having a carboxy group. Non-limiting examples thereof include silver salts of an aliphatic carboxylic acid and a silver salt of an aromatic carboxylic acid. Preferred examples of the silver salts of aliphatic carboxylic acids include silver behenate, silver stearate, silver oleate, silver laurate, silver caproate, silver myristate, silver palmitate, silver maleate, silver fumarate, silver tartrate, silver linoleate, silver butyrate and silver camphorate, mixtures thereof, etc. Silver salts with a halogen atom or a hydroxyl on the aliphatic carboxylic acid can also be effectively used. Preferred examples of the silver salts of aromatic carboxylic acids and other carboxyl group-containing compounds include silver benzoate, a silver substituted benzoate such as silver 3,5-dihydroxybenzoate, silver o-methylbenzoate, silver m-methylbenzoate, silver p-methylbenzoate, silver 2,4-dichlorobenzoate, silver acetamidobenzoate, silver p-phenyl benzoate, etc., silver gallate, silver tannate, silver phthalate, silver terephthalate, silver salicylate, silver phenylacetate, silver pyromellitate, a silver salt of 3-carboxymethyl-4-methyl-4-thiazoline-2-thione or the like as described in U.S. Pat. No. 3,785,830, and silver salt of an aliphatic carboxylic acid containing a thioether group as described in U.S. Pat. No. 3,330,663, etc.

Silver salts of compounds containing mercapto or thione groups and derivatives thereof can also be used. Preferred examples of these compounds include a silver salt of 3-mercapto-4-phenyl-1,2,4-triazole, a silver salt of 2-mercaptobenzimidazole, a silver salt of 2-mercapto-5-aminothiadiazole, a silver salt of 2-(ethylglycolamido) benzothiazole, a silver salt of thioglycolic acid such as a silver salt of an S-alkyl thioglycolic acid (wherein the alkyl group has from 12 to 22 carbon atoms), a silver salt of a dithiocarboxylic acid such as a silver salt of dithioacetic acid, a silver salt of a thioamide, a silver salt of 5-carboxylic-1-methyl-2-phenyl-4-thiopyridine, a silver salt of mercaptotriazine, a silver salt of 2-mercaptobenzoxazole, a silver salt as described in U.S. Pat. No. 4,123,274, for example, a silver salt of 1,2,4-mercaptothiazole derivative such as a silver salt of 3-amino-5-benzylthio-1,2,4-thiazole, a silver salt of thione compound such as a silver salt of 3-(2-carboxyethyl)-4-methyl-4-thiazoline-2-thione as disclosed in U.S. Pat. No. 3,301,678.

Furthermore, a silver salt of a compound containing an imino group may be used. Preferred examples of these compounds include silver salts of benzothiazole and derivatives thereof, for example, silver salts of benzothiazoles such as silver methylbenzotriazolate, etc., silver salt of halogen-substituted benzotriazoles, such as silver 5-chlorobenzotriazolate, etc., silver salts of carboimidobenzotriazole, etc., silver salt of 1,2,4-triazoles or 1-H-tetrazoles as described in U.S Pat. No. 4,220,709, silver salts of imidazoles and imidazole derivatives, and the like. Various silver acetylide compounds can also be used, for instance, as described in U.S. Pat. Nos. 4,761,361 and 4,775,613.

It is also found convenient to use silver half soaps, of which an equimolar blend of silver behenate and behenic acid, prepared by precipitation from aqueous solution of the sodium salt of commercial behenic acid and analysing about 14.5 percent silver, represents a preferred example.

The method used for making silver soap dispersions is well known in the art and is disclosed in Research Disclosure, April 1983, item 22812, *Research Disclosure*, October 1983, item 23419 and U.S. Pat. No. 3,985,565.

The light-sensitive silver halides may be advantageously spectrally sensitized with various known dyes including cyanine, merocyanine, styryl, hemicyanine, oxonol, hemioxonol and xanthene dyes. Useful cyanine dyes include those having a basic nucleus, such as a thiazoline nucleus, an oxazoline nucleus, a pyrroline nucleus, a pyridine nucleus, an oxazole nucleus, a thiazole nucleus, a selenazole nucleus and an imidazole nucleus. Useful merocyanine dyes which are preferred include those having not only the above described basic nuclei but also acid nuclei, such as a thiohydantoin nucleus, a rhodanine nucleus, an oxazolidinedione nucleus, a thiazolidinedione nucleus, a barbituric acid nucleus, a thiazolinone nucleus, a malononitrile nucleus and a pyrazolone nucleus. In the above described cyanine and merocyanine dyes, those having imino groups or carboxyl groups are particularly effective. Practically, the sensitizing dyes to be used in the present invention may be properly selected from known dyes such as those described in U.S. Pat. Nos. 3,761,279, 3,719,495, and 3,877,943, British Patents Nos. 1,466,201, 1,469,117 and 1,422,057, and can be located in the vicinity of the photocatalyst according to known methods. Spectral sensitizing dyes may be typically used in amounts of about $10^{-4}$ mol to about 1 mol per 1 mol of silver halide.

In addition to the aforementioned ingredients it may be advantageous to include additives known as "toners" that improve the image. Toner materials may be present, for example, in amounts from 0.1 to 10 percent by weight of all silver bearing components. Toners are well known materials in the photothermographic art as shown in U.S. Pat. Nos. 3,080,254, 3,847,612 and 4,123,282.

Examples of toners include phthalimide and N-hydroxyphthalimide; cyclic imides such as succinimide, pyrazoline-5-ones, and a quinazolinone, 3-phenyl-2-pyrazoline-5-one, 1-phenylurazole, quinazoline, and 2,4-thiazolidinedione; naphthalimides (e.g., N-hydroxy-1,8-naphthalimide); cobalt complexes (e.g., cobaltic hexamine trifluoroacetate); mercaptans as illustrated by 3-mercapto-1, 2,4-triazole, 2,4-dimercaptopyrimidine, 3-mercapto-4,5-diphenyl-1,2, 4-triazole and 2,5-dimercapto-1,3,4-thiadiazole; N-(aminomethyl)aryldicarboximides, (e.g., (N,N-dimethylam inomethyl)phthalimide, and N,N-(dimethylaminomethyl) naphthalene-2,3-dicarboximide); and a combination of blocked pyrazoles, isothiuronium derivatives and certain photobleaching agents (e.g., a combination of N,N'-hexamethylene bis(1-carbamoyl-3,5-dimethylpyrazole), 1,8-(3,6-diazaoctane)bis(isothiuronium trifluoroacetate) and 2-(tribromomethylsulfonyl) benzothiazole); and merocyanine dyes such as 3-ethyl-5[(3-ethyl-2-benzo thiazolinylidene)-1-methylethylidene]-2-thio-2,4-oxazolidinedione; phthalazine and phthalazinone derivatives or metal salts of these derivatives such as 4-(1-naphthyl)phthalazinone, 6-chlorophthalazinone, 5,7-dimethoxyphthalazinone, and 2,3-dihydro-1,4-phthalazinedione; phthalic acid derivatives (e.g., phthalic acid, 4-methylphthalic acid, 4-nitrophthalic acid, and tetrachlorophthalic anhydride); quinazolinediones, benzoxazine or naphthoxazine derivatives; rhodium complexes functioning not only as tone modifiers, but also as sources of halide ion for silver halide formation in situ, such as ammonium hexachlororhodate (III), rhodium bromide, rhodium nitrate and potassium hexachlororhodate (III); inorganic peroxides and persulfates (e.g., ammonium peroxydisulfate and hydrogen peroxide); benzoxazine-2,4-diones such as 1,3-benzoxazine-2,4-dione,8-methyl-1,3-benzoxazine-2,4-di one, and 6-nitro-1,3-benzoxazine-2,4-dione; pyrimidines and asymmetric triazines (e.g., 2,4-dihydroxypyrimidine, 2-hydroxy-4-aminopyrimidine), azauracils, and tetrazapentalene derivatives (e.g, 3,6-dimercapto-1,4-diphenyl-1H, 4H-2,3a,5,6a-tetrazapentalene, and 1,4-di(o-chlorophenyl)-3,6-dimercapto-1H, 4H-2,3a,5,6a-tet razapentalene).

Silver halide emulsions can be protected against the additional production of fog and can be stabilized against loss of sensitivity during shelf storage. Suitable antifoggants, stabilizers, and stabilizer precursors which can be used alone or in combination, include thiazolium salts as described in U.S. Pat. Nos. 2,131,038 and 2,694,716; azaindenes as described in U.S. Pat. Nos. 2,886,437 and 2,444, 605; mercury salts as described in U.S. Pat. No. 2,728,663; urazoles as described in U.S. Pat. No. 3,287,135; sulfocatechols as described in U.S. Pat. No. 3,235,652; oximes as described in British Patent No. 623448; nitrones; nitroindazoles; polyvalent metal salts as described in U.S. Pat. No. 2,839,405; thiouronium salts as described in U.S. Pat. No. 3,220,839; and palladium, platinum and gold salts described in U.S. Pat. Nos. 2,566,263 and 2,597,915; halogen-substituted organic compounds as described in U.S. Pat. Nos. 4,108,665 and 4,442,202; triazines as described in U.S. Pat. Nos. 4,128,557; 4,137,079; 4,138,265; and 4,459,350; and phosphorous compounds as described in U.S. Pat. No. 4,411,985.

Emulsions of the invention can contain plasticisers and lubricants such as polyalcohols (e.g., glycerin and diols of the type described in U.S. Pat. No. 2,960,404); fatty acids or esters such as those described in U.S. Pat. No. 2,588,765 and U.S. Pat. No. 3,121,060; and silicone resins such as those described in British Patent No. 955061.

The photothermographic elements of the present invention may include image dye stabilizers. Such image dye stabilizers are illustrated by British Patent No. 1326889; U.S. Pat. Nos. 3,432,300; 3,698,909; 3,574,627; 3,573,050; 3,764,337 and 4,042,394.

Photothermographic elements containing emulsion layers according to the present invention can be used in photographic elements which contain light absorbing materials and filter dyes such as those described in U.S. Pat. Nos. 3,253,921; 2,274,782; 2,527,583 and 2,956,879. If desired, the dyes can be mordanted, for example, as described in U.S. Pat. No. 3,282,699.

Photothermographic elements containing emulsion layers as described herein can contain matting agents such as starch, titanium dioxide, zinc oxide, silica, polymeric beads including beads of the type described in U.S. Pat. No. 2,992,101 and U.S. Pat. No. 2,701,245.

Emulsions in accordance with this invention can be used in photothermographic elements which contain antistatic or conducting layers, such as layers that comprise soluble salts (e.g., chlorides, nitrates, etc.), evaporated metal layers, ionic polymers such as those described in U.S. Pat. Nos. 2,861, 056 and 3,206,312 or insoluble inorganic salts such as those described in U.S. Pat. No. 3,428,451.

The binder may be selected from any of the well-known natural or synthetic resins such as, polyvinyl acetals, polyvinyl chloride, polyvinyl acetate, cellulose acetate, polyolefins, polyesters, polystyrene, polyacrylonitrile, polycarbonates, and the like. Copolymers and terpolymers are of course included in these definitions. The preferred binders are oleophilic polymers such as polyvinyl butyral, butyl ethyl cellulose, methacrylate copolymers, maleic anhydride ester copolymers, polystyrene, and butadiene-styrene copolymers.

Optionally, these polymers may be used in combinations of two or more thereof. Such a polymer is used in an amount sufficient to carry the components dispersed therein, that is, within the effective range of the action as the binder. The effective range can be appropriately determined by one skilled in the art. As a guide in the case of carrying at least an organic silver salt, it can be said that a preferable ratio of the binder to the organic silver salt ranges from 15:1 to 1:2, and particularly from 8:1 to 1:1.

The formulation for the photothermographic emulsion layer can be prepared by dissolving or dispersing the photosensitive silver halide, the source or reducible silver, the redox colour releasing compounds, optional additives, and the binder in an inert organic solvent, such as, for example, acetone, 2-butanone or tetrahydrofuran.

The formulation can be coated onto a support by methods well known in the art, such as, for example, wire-wound rod, knife, or extrusion coatings. Typical wet thickness of the emulsion layer can range from about 10 to about 150 micrometers (μm), and the layer can be dried in forced air at temperatures ranging from 20° C. to 100° C. It is preferred that the thickness of the layer be selected to provide maximum image densities greater than 0.2, and more preferably in the range 0.5 to 2.5, as measured by a MacBeth Colour Densitometer Model TD 504 using the colour filter complementary to the dye colour.

Alternatively, the formulation may be spray dried to produce solid particles, which can then be redispersed in a second, possibly different, binder and then coated onto the support.

The formulation for the emulsion layer can also include coating aids such as fluoroaliphatic polyesters.

The support or substrate of the photothermographic element can be selected from a wide range of materials, including paper, glass, metal, polymeric film, and the like, depending upon the particular imaging requirement. Preferred materials for the support include polymers having good heat stability, such as polyesters. A particularly preferred polyester is polyethylene terephthalate.

Barrier layers, preferably comprising a polymeric material, can also be present in the photothermographic element of the present invention. Polymers for the material of the barrier layer can be selected from natural and synthetic polymers such as gelatin, polyvinylalcohols, polyacrylic acids, sulfonated polystyrene, and the like. The polymers can optionally be blended with barrier aids such as silica.

Images derived from the photothermographic element are typically transferred to an image receiving layer. The image receiving layer of this invention can be any flexible or rigid, transparent layer made of thermoplastic polymer. The image receiving layer preferably has a thickness of at least 0.1 micrometers, and a glass transition temperature of from about 20° C. to about 200° C. In the present invention, any thermoplastic polymer or combination of polymers can be used, provided the polymer is capable of absorbing the dye. Because the polymer acts as a dye mordant, no additional fixing agents are required. Thermoplastic polymers that can be used to prepare the image receiving layer include polyesters, such as polyethylene terephthalates, polyolefins, such as polyethylene, cellulosics, such as cellulose acetate, cellulose acetate butyrate, cellulose acetate propionate, polystyrene, polyvinyl chloride, polyvinylidene chloride, polyvinyl acetate, copolymer of vinylchloride-vinylacetate, copolymer of vinylidene chloride-acrylonitrile, copolymer of styrene-acrylonitrile, and the like.

The optical density of the dye image and even the actual colour of the dye image in the image receiving layer is very much dependent on the characteristics of the polymer of the image receiving layer, which acts as a dye mordant, and, as such, is capable of absorbing and fixing the dyes. A dye image having a reflection optical density in the range of from 0.3 to 3.5 (preferably from 1.5 to 3.5) or a transmission optical density in the range of from 0.2 to 2.5 (preferably from 1.0 to 2.5) can be obtained with the present invention.

The image receiving layer can be formed by dissolving at least one thermoplastic polymer in an organic solvent (e.g. 2-butanone, acetone, tetrahydrofuran) and applying the resulting solution to a support base or substrate by various coating methods known in the art, such as curtain coating, extrusion coating, dip coating, air-knife coating, hopper coating, and any other coating method used for coating solutions. After the solution is coated, the image receiving layer is dried (e.g. in an oven) to drive off the solvent. The image receiving layer may be strippably adhered to the photothermographic element. Strippable image receiving layers are described in U.S. Pat. No. 4,594,307, incorporated herein by reference.

Selection of the binder and solvent to be used in preparing the emulsion layer significantly affects the strippability of the image receiving layer from the photosensitive element. Preferably, the polymer for the image receiving layer is impermeable to the solvent used for coating the emulsion layer. The selection of the preferred binders and solvents results in weak adhesion between the emulsion layer and the image receiving layer and promotes good strippability of the emulsion layer.

The photothermographic element can also include coating additives to improve the strippability of the emulsion layer. For example fluoroaliphatic polyesters dissolved in ethyl acetate can be added in an amount of from about 0.02 to about 0.5 weight percent of the emulsion layer, preferably from about 0.1 to about 0.3 weight percent. A representative example of such a fluoroaliphatic polyester is "Fluorad FC 431", commercially available from Minnesota Mining and Manufacturing Company. Alternatively, a coating additive can be added to the image receiving layer in the same weight range to enhance strippability. No solvents need to be used in the stripping process. The strippable layer preferably has a delaminating resistance of 1 to 50 g/cm and a tensile strength at break greater than, preferably at least two times greater than, its delaminating resistance.

Preferably, the image receiving layer is adjacent to the emulsion layer to facilitate transfer of the dye that forms after the imagewise exposed emulsion layer is subjected to thermal development, for example, in a heated shoe and roller type heat processor.

In another embodiment, the coloured dye released in the emulsion layer can be transferred onto a separately coated image receiving sheet by placing the exposed emulsion layer in intimate face-to-face contact with the image receiving sheet and heating the resulting composite construction. Good results can be achieved in this second embodiment when the layers are in uniform contact for a period of time of from 0.5 to 300 seconds at a temperature of from about 80° C. to about 220° C.

Multi-colour images can be prepared by superimposing in register, imaged image receiving layers as prepared above. The polymers of the individual imaged image-receiving layers must be sufficiently adherent to provide useful multi-colour reproduction on a single substrate.

Alternatively, a multi-colour image may be prepared by contacting a single image receiving sheet successively with two or more imagewise exposed photothermographic emulsion layers which release dyes of different colours, and heating to transfer the released dyes as described above. This method is particularly suitable for the production of colour proofs, especially when the dyes released by the photothermographic emulsions have hues which match the internationally agreed standards for colour reproduction (SWOP colours). Dyes with this property are disclosed in U.S. Pat. No. 5,023,229. In this embodiment, the photothermographic emulsions preferably comprise compounds of Formula I, i.e. operate via preformed dye release, as this enables the image dye absorptions to be tailored more easily to particular requirements. Also in this embodiment, the emulsions are preferably all sensitised to the same wavelength range regardless of the colour of dye released. For example, they may be sensitised to UV radiation with a view to contact exposure on conventional printing frames, or they may be sensitised to longer wavelengths, especially red or near infrared, to enable digital address by lasers.

Alternatively, multi-colour images can be produced from a photothermographic element comprising a substrate, an image receiving layer, and two or more photothermographic layers capable of forming different colours in response to light exposure and thermal development, said photothermographic layers being sensitive to different wavelengths of light, and at least one of said photothermographic layers comprising a redox colour releasing compound of the invention. Each photothermographic layer may be sensitised to a wavelength range related to the colour released by that layer, or alternatively it may be sensitised to an unrelated wavelength, e.g. in the infrared. The latter embodiment facilitates selective address of an individual layer by a laser modulated in accordance with image information for that layer. The technique, known as false colour address, is described in numerous patents, e.g. U.S. Pat. No. 4,705,745. The various layers may be coated sequentially by the methods outlined above, optionally with barrier layers separating the light sensitive layers in order to minimise migration of active ingredients among the layers, which would lead to crosstalk.

Another method of minimising crosstalk between the layers is to coat each light sensitive layer on a separate carrier sheet and laminate them sequentially on the final substrate, i.e. on top of the image receiving layer. Subsequent to the lamination of each light sensitive layer, its associated carrier sheet is peeled off and discarded before lamination of the next layer. Lamination is readily carried out using a heated roller device, such as MATCHPRINT Laminator, with roller temperatures in the range 100° to 275° F. Suitable materials for the carrier sheets include polyester of thickness 25 to 200 microns, optionally treated with a release agent such as FLUORAD FC 431 to facilitate peeling.

Development conditions will vary, depending on the construction used, but will typically involve heating the imagewise exposed material at a suitably elevated temperature, e.g. from about 80° C. to about 250° C., preferably from about 120° C. to about 200° C., for a sufficient period of time, generally from 1 second to 2 minutes.

In some methods, the development is carried out in two steps. Thermal development takes place at a higher temperature, e.g. about 150° C. for about 10 seconds, followed by thermal diffusion at a lower temperature, e.g. 80° C., optionally in the presence of a transfer solvent. The second heating step at the lower temperature prevents further development and allows the dyes that are already formed to diffuse out of the emulsion layer.

The material of this invention can be used for example, in conventional colour photography, in electronically generated colour hardcopy recording, and in digital colour proofing in the graphic arts area. The material of this invention provides high photographic speed, provides pure dye images, and provides a dry and rapid process.

The following is an explanation of abbreviations, trade names and chemical structures referred to in the Examples:

Basic Blue 3

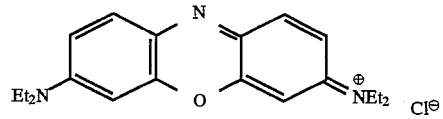

(available from Aldrich Chemical Co.)

BB3    denotes the leuco form of Basic Blue 3 functionalised at the 1-position, i.e.:-

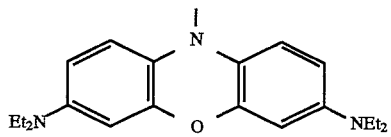

Compounds A–L

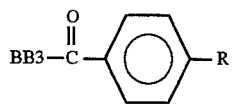

| | |
|---|---|
| $R = -O-\overset{O}{\underset{\|}{C}}-CH_3$ | Compound A |
| R = —OH | Compound B |
| R = —H | Compound D |
| R = —CH$_3$ | Compound E |
| R = —O—(CH$_2$)$_8$—OH | Compound G |
| R = —O—(CH$_2$)$_{11}$—OH | Compound H |

Compound C

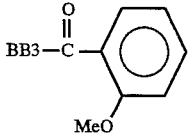

-continued
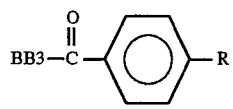
| | |
|---|---|
| Compound F | 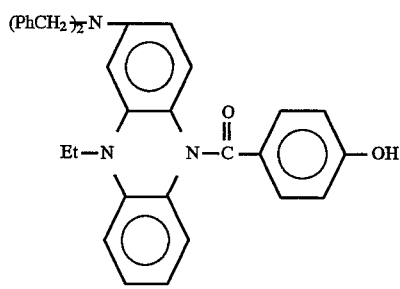 |
| Compound I | 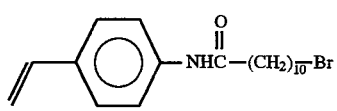 |
| Compound J | 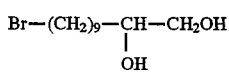 |
| Compound K | 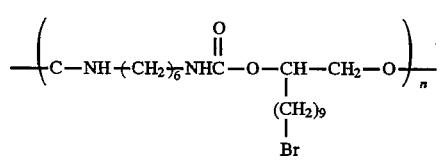 |
| Compound L | 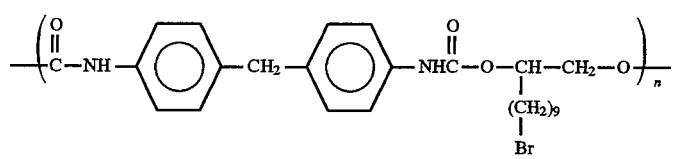 |
| Dye (1) | 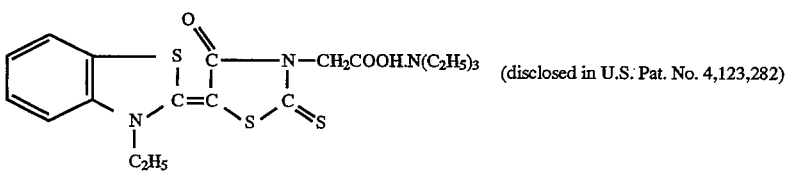 (disclosed in U.S. Pat. No. 4,123,282) |
| Dye (2) | 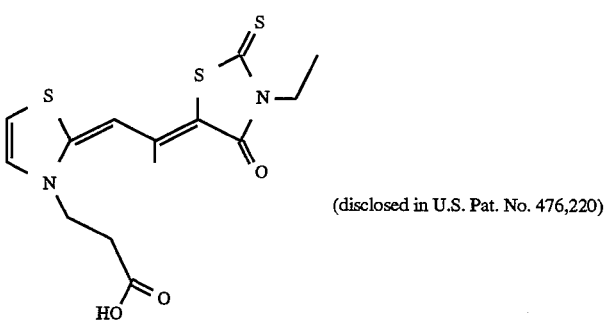 (disclosed in U.S. Pat. No. 476,220) |

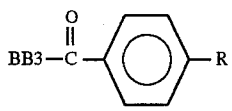

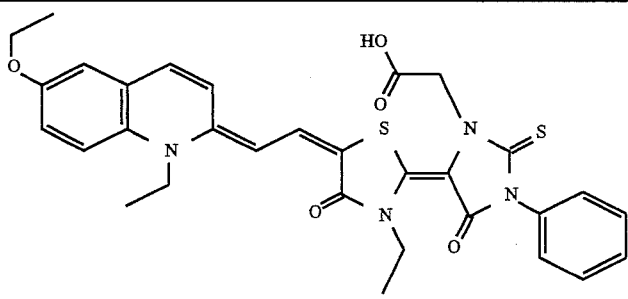

Dye (3)

(disclosed in U.S. Pat. No. 3,719,495)

Butvar B—72 Polyvinylbutyral (Monsanto)
VYNS—Copolymer of vinyl acetate and vinyl chloride (Union Carbide)
PVC—Polyvinyl chloride
Fluorad™FC431—Fluorinated surfactant (3M)
THF Tetrahydrofuran
4-MPA—4-methylphthalic aid
DBTDL—dibutyltin dilaurate
Hyflo—Filter aid
IPA—Propan-2-ol
VROH—Copolymer of vinyl chloride and vinyl acetate (partially hydrolysed) (Union Carbide)
PVAL—Polyvinylacetal
PVOH—Polyvinylalcohol The present invention will be illustrated in detail in the following examples, but the embodiment of the present invention is not limited thereto.

EXAMPLE 1

4.1 Typical Procedure for Preparation of Dimers incorporating dye at final stage Preparation of 1,5-bis((2'-methoxycarbonyl) phenoxypentane Methyl salicylate (117.4 g, 0.77 mol) and 1,5-diiodopentane (100 g, 0.31 mol) in dry acetone (1.5 liter) were treated with anhydrous potassium carbonate (213 g, 1.54 mol). The mixture was heated at reflux for 16 hours. The reaction was allowed to cool, then filtered. The filtrate was evaporated and the resulting pale yellow oil distilled to remove excess methyl salicylate. The residue was washed with 40 to 60 petroleum ether (4×500 ml), the petrol was decanted off between washes. The last of the petrol was removed by rotary evaporation to give the bis(ether) as a colourless oil (72.71 g, 62%).

Preparation of 1,5-bis((2'carboxy)phenoxy)pentane

The bis(ester) (72.71 g, 0.195 mol) in ethanol (1 liter) was treated with KOH (43 g, 0.78 mol) and water (20 ml). The mixture was heated at reflux for 16 hours. The mixture was cooled and the resulting precipitate was filtered off and dried in vacuo. Once dry the solid was dissolved in water and the resulting solution was acidified with 12N HCl. The precipitated solid was filtered off and dried in vacuo to give the bis(acid) as a colourless solid (55.28 g, 82%) m.p. 105°–6° C.

Preparation of 1,5-bis((2'-chlorocarbonyl)phenoxy) pentane

The bis(acid) (53 g, 0.154 mol) was heated at reflux in thionyl chloride (150 ml) for 2 hours. The excess thionyl chloride was distilled off and 40 to 60 petroleum ether was added to the resulting gum. The solid which precipitated was filtered off to give the acid chloride as a colourless solid (55 g, 94%).

Preparation of 1,5-bis((2'-(3",7"-bis(N,N-diethylamino) phenoxazin-10"-yl)carbonyl) phenoxy)pentane (Compound No. 1)

Basic Blue 3 (73.2 g, 204 mmol, 85%, Aldrich Co.,) in dichloromethane (500 ml) was overlaid with water (1.5 liter). Sodium dithionite (74 g) was added. The mixture was stirred at room temperature with careful monitoring of the pH of the aqueous layer, ensuring that the pH was maintained between 5 and 7 at all times. Once the colour of the organic layer had changed from blue to yellow, the bis(acid chloride) (30 g, 79 mmol) in dichloromethane (70 ml) was added directly to the organic layer via a pipette. The mixture was stirred at room temperature for a further 2 hours. The layers were separated and the organics were dried over $MgSO_4$, filtered and evaporated. The residue was adsorbed onto silica and washed through a pad of silica gel 60 (120 g) with ether (4 liters) to remove the excess basic blue 3. The filtrate was evaporated to give the dimeric leuco as a pale green powder (49.87 g, 66%), m.p. 104°–7° C.

Typical Procedure for Preparation of Dimer from Functionalised Dye

Preparation of 3,7-bis(N,N-diethylamino)-10-(4'-acetoxybenzoyl)phenoxazine (Compound A)

Basic Blue 3 (85 g, 201 mmol) was dissolved in dichloromethane (1 liter), water (1.2 liter) was added and the pH was adjusted to 6 using 10M sodium hydroxide solution. Sodium dithionite (85 g) was added to the mixture and the layers separated in the reaction vessel. The pH of the aqueous layer was monitored continuously throughout the reaction and 10M NaOH was added to maintain the pH between 5 and 7. Once the dye had been reduced (ca. 30 minutes), 4-acetoxybenzoyl chloride (40 g, 201 mmol) in dichloromethane (200 ml) was added directly to the organic layer. The mixture was stirred at room temperature for 2.5 hours. The layers were separated and the organics were dried, filtered and evaporated to give 130 g of a blue/green oil. This was recrystallised from ethanol to give 54.9 g (55%) of the desired leuco m.p. 122°–3° C.

Preparation of 3,7-bis(N,N-diethylamino)-1-(4'-hydroxybenzoyl)phenoxazine (Compound B)

The acetate (Compound A) (60 g, 123 mmol) was dissolved in methanol (1.3 liter) warmed to 50° C. Potassium hydroxide (6.9 g, 123 mmol) was added and the mixture stirred at this temperature for 16 hours. The mixture was cooled and the solution was evaporated. The residue was taken up into ethyl acetate and the undissolved potassium acetate filtered off. Silica (ca 50 g) was added and then filtered off, the filtrate was evaporated and dried in vacuo to give 39.6 g (67%) of the phenol (Compound B).

Preparation of 1,6-bis(4'-(3",7"-bis(N,N-diethylamino) phenoxazin-10"-yl) carbonylphenoxy)hexane (Compound No. 5)

Compound B (6.06 g, 14.5 mol), 1,6-diiodohexane (2.45 g, 7.26 mmol) and anhydrous caesium carbonate (5.2 g, 16 mmol) were heated in dry acetone for 64 hours. The mixture was cooled and then filtered. The filtrate was evaporated and the solid boiled with ethanol and filtered off to give 6.1 g (86%) of the dimer (Compound No. 5) as a yellow solid.

Compounds 2 to 4 and 6 to 10 were prepared by methods similar to those employed for Compounds 1 and 5.

Diffusion Tests

Test (a)

The following construction of photothermographic element was employed:

photosensitive layer
barrier layer (when present)
receptor layer
base

A polyester base was sprayed with a fluorinated surfactant and the receptor layer comprising VYNS coated at 75 μm (wet thickness).

Elements were prepared with:

a) no barrier layer, b) a Butvar B72 barrier layer coated at 50 μm (wet thickness) (5% solids), and c) a poly(vinyl acetal) coated at 25 μm (wet thickness) (2% solids).

| The formulation of the photosensitive layer was: | |
|---|---|
| Halidised soap | 15 g |
| Dye (1) (0.04%) | 0.75 ml |
| 4-methylphthalic acid (10% in EtOH) | 1.5 ml |
| Test compound (in toluene (1.5 ml)) | 0.32 mmol |

The above formulation was coated at 75 μm (wet thickness) onto a polyester base sprayed with fluorinated surfactant and laminated onto the receptor or barrier layer.

The compounds tested were Compound No. 1 and 3,7-bis(N,N-diethylamino)-1-(2'-methoxybenzoyl)phenoxazine (Compound C).

The samples were thermally processed at 135° C. and the percentage of Test Compound transferred to the receptor layer measured spectrophotometrically at different times. The following Table summarises the results after 30 seconds processing time.

| Construction | Compound C | Compound No. 1 |
|---|---|---|
| No barrier layer | 52 | 47 |
| Butvar B72 barrier | 47 | 31 |
| Poly(vinyl acetal) barrier layer | 46 | 39 |

This test which demonstrates the mobility of the Compounds between two adjacent layers shows that at a processing temperature of 135° C. 53% of the leuco dye (Compound No. 1) remained in the soap layer compared with 48% for Compound C. The use of a Butvat B72 barrier layer between the receptor and the soap layer increases the differential. In this case 31% of the dimer (Compound 1) diffuses through to the receptor layer, compared to 47% of the "monomer" (Compound C). When the barrier layer is changed to a poly(vinyl acetal) the figures are 39% and 46% respectively.

Test (b)

The Compounds were tested in an element of the following construction:

photosensitive layer
PVC interlayer
blank soap layer
receptor layer
base

The constitution of the layers was as follows:

Receptor Layer: A 15 wt % solution of a copolymer of vinylchloride (90 mol %) and vinyl acetate (10 mol %) (U CAR VYNS-3, Union Carbide) in a mixture of toluene (50 wt %) and butanone (50 wt %) was coated onto an opaque polyester film (Melinex 994, ICI) and dried in an oven at 80° C.

The soap was prepared in the following manner.

A dispersion of silver behenate half soap (silver behenate (1 mol) and behenic acid (1 mol) 10 wt % solids) in a mixture of toluene (10 wt %) and ethanol (90 wt %) was made by a homogenisation process. 110 g of this 10 wt % half soap dispersion was diluted with ethanol (340 g) and 2-propanol (10 g). Butvar B-72 (0.4 g) was added to this stirred dispersion, followed by mercuric bromide (0.18 g) in ethanol (10 ml). This was followed by the addition of a further quantity of Butvar B-72 (26 g).

For the blank soap layer 3 drops of Fluorad FC431 fluorinated surfactant was added.

For the photosensitive layer the dispersion was treated as follows.

The test Compound (0.42 mmol of a monomeric leuco or 0.21 mmol of a dimeric) in toluene (3 ml), dye (1) (1 ml of a solution containing 0.5 mg in a mixture of toluene (150 ml) and methanol (50 ml)) and 4-methylphthalic acid (0.5 mmol) were added to 25 g of the dispersion.

The Compounds tested were:

3,7-bis(N,N-diethylamino)-1-(benzoyl)phenoxazine (Compound D), 3,7-bis(N,N-diethylamino)-1-(4'-methylbenzoyl) phenoxazine (Compound E), and Compound 10.

Interlayer: 3.5 wt % of PVC in THF.

The receptor layer was coated to a wet thickness of 80 μm, the blank soap layer was coated at a thickness of 80 μm onto the dried receptor layer. Once dry, this was overcoated with the interlayer at a thickness of 80 μm. This was dried and then coated with the photosensitive layer at a thickness of 130 μm.

The diffusion test was carried out by imagewise exposure of the strip and thermal processing at 140° C. for 30 seconds. The photosensitive layers were stripped away from the receptor layer. A solution of N-bromosuccinimide (one drop of a solution of 0.72 g in acetone/toluene (100 ml of a 1:1 mixture) was dropped onto an area with no dye transferred (Dmin). This serves to oxidise any leuco dye present. The optical densities of the cyan dye formed in the treated area was measured using a reflection densitometer with a red filter. The results are summarised in the following Table.

| Compound | Density |
| --- | --- |
| D | 1.17 |
| E | 1.07 |
| 10 | 0.17 |

The monomeric dyes, pergascript turquoise (Compound D) and Compound E gave spots of density 1.17 and 1.07 respectively, whilst the dimer gave a spot with a density of 0.17. This shows that there is a significant reduction in mobility for the dimeric compounds of the invention.

Sensitometry

Photothermographic elements having the following different photosensitive layers were prepared.

Formulation 1

| | |
| --- | --- |
| Halidised soap | 15 g |
| Dye (2) (0.04% w/v in EtOH) | 1 ml |
| Test compound | 0.1 mmol |
| Toluene | 1 ml |
| 4-Methylphthalic acid | 0.1 g |
| Ethanol | 1 ml |

The above soap was coated at 75 μm (wet thickness) onto a VYNS receptor layer containing 5 drops of FC 431, fluorinated surfactant.

Formulation 2

| | |
| --- | --- |
| Halidised soap | 10 g |
| Dye (1) (0.02%) | 1 ml |
| Compound No. 3 in $CH_2Cl_2$ (0.12 g/ml) | 1 ml |
| 4-methylphthalic acid in MeOH | 0.3 g in 1.5 ml |

The above soap was coated at 75 μm (wet thickness) onto a receptor layer of VYNS.

Formulation 3

As described in Test (b) above incorporating Compound No. 10.

All elements were exposed for 1/1000th of a second on an EG and G sensitometer. Elements of Formulation 1 were exposed through a Wratten No. 58 filter and the others through a Wratten No. 25 red filter. Elements of Formulation 1 and 2 were thermally processed at 135° C. for 30 seconds on a hot block. The element of Formulation 3 was heated on a blanket at 140° C. for 30 seconds.

The Dmin and Dmax of the elements were measured, the elements of Formulation 1 for the full construction and those of the other formulations after the receptor had been peeled-apart. The results are reported in the following Table.

| Compound | 1 | 3 | 4 | 5 | 6 |
| --- | --- | --- | --- | --- | --- |
| Formulation | 1 | 2 | 1 | 1 | 1 |
| Dmin | 0.22 | 0.82 | 0.70 | 0.13 | 0.09 |
| Dmax | 1.71 | 1.14 | 1.86 | 1.95 | 0.47 |
| Compound | 7 | 8 | 9 | 10 | |
| Formulation | 1 | 1 | 1 | 3 | |
| Dmin | 0.20 | 0.12 | 1.00 | 0.12 | |
| Dmax | 2.03 | 0.65 | 1.68 | 1.86 | |

Thus, not only do the dimeric compounds show reduced mobility, they also exhibit photothermographic behaviour. It will be appreciated none of the data quoted are for optimised formulae but serve to illustrate the photothermographic behaviour of the compounds tested.

EXAMPLE 2

Preparation of 1,3,5,7-tetra(11'-bromoundecan-1-yl) tetramethytcyclotetra-siloxane A degassed solution of redistilled 1,3,5,7-tetramethylcyclotetrasiloxane (Huls America Inc.) 4.98 mmol) and 11-bromo-1-undecene (4.9 g, 21 mmol) in toluene (5 ml) was treated with a solution of platinum divinyl teramethylsiloxane in xylene (Huls America Inc.) (0.02 ml). The mixture was heated at 60° C. for 20 minutes under nitrogen. After this time IR spectroscopy showed that the reaction had proceeded to completion. The mixture was evaporated and the residue chromatographed over silica gel using 40–60 petrol as eluent until all the unreacted alkene had eluted and then eluting with ether to give the tetrakis (alkyl bromide) (4.50 g, 77%) as a colourless oil.

Preparation of Compound No. 11

The above tetrakis(alkyl bromide) (1.125 g, 1 mmol), Compound B (2.27 g, 5.1 mmol) and caesium carbonate (1.95 g, 6 mmol) were heated at reflux under nitrogen in dry THF for 72 hours. The mixture was cooled to room temperature and then filtered. The filtrate was evaporated and the residue was taken up into ether and washed with brine. The organics were separated, dried, filtered and evaporated to give a yellow foam. The foam was washed with ethanol (2×100 ml) and then boiled with ethanol (2×200 ml), taken into ether and evaporated to give the Compound No. 11 as a yellow foam (1.7 g, 64%).

Preparation of Tetrameric Compound No. 12

The above tetrakis(alkyl bromide)(3)(1.125 g, 1 mmol), Compound F (2.31 g, 4.4 mmol) and caesium carbonate (1.93 g, 6 mmol) were heated in dry THF for 96 hours under argon. The mixture was cooled and the solvent evaporated. The residue was partitioned between ethyl acetate and water. The organics were separated, dried, filtered and evaporated to give a brown solid. The solid was boiled with ethanol (5×125 ml) and then taken up into dichloromethane. The solution in dichloromethane was added dropwise to ethanol to precipitate Compound No. 12 as a pale brown solid (0.95 g, 32%).

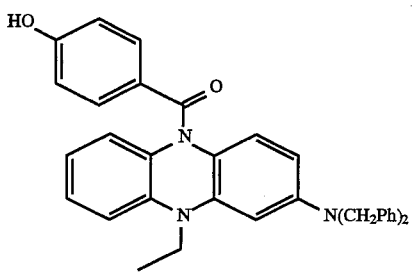

Compound F

Photothermographic Elements

The construction of the elements was as follows:
photosensitive layer
barrier layer (when present)
receptor layer
base The base was coated with a receptor layer of VYNS (15% MEK/toluene) at 75 µm wet thickness. The barrier layer, when present was poly(vinyl acetal) (2% MeOH) at 24 µm wet thickness.

The formulation of the photosensitive layer was:

| | |
|---|---|
| Halidised soap | 5 g |
| Dye (1) (0.04%) | 0.5 ml |
| 4-MPA | 40 mg |
| EtOH | 1 ml |
| Test Compound | 72 mg |
| Toluene | 1 ml |

Halidisation of soap

| | | Mixing Time |
|---|---|---|
| 11% 1/2 soap homogenate (EtOH) | 100 g | |
| Ethanol | 114 g | 15 minutes |
| Butvar B72 (10% w/w EtOH) | 20 g | |
| HgBr$_2$ (36 mg/ml) | 1.9 ml | 60 minutes |
| Zn Br$_2$ (22.5 mg/ml) | 1.9 ml | 120 minutes |
| Butvar B72 | 12.7 g | 120 minutes |
| FC 431 | 0.74 g | 15 minutes |

The photosensitive layer was either applied by solvent coating or was coated onto polyester treated with a fluorinated surfactant and thereafter laminated onto the barrier/receptor layer.

The Compounds tested were Compound No. 11 and Compound C.

Diffusion Tests

Compound No. 11 was shown to diffuse into a receptor layer adjacent to the photosensitive layer in which it was coated to a lesser degree than Compound C. In both laminated and solvent coated samples 13% of the Compound No. 11 had diffused into the receptor layer after 10 seconds at 135° C. This result compares with 43% of Compound C under similar conditions. Incorporation of the barrier layer between the photosensitive layer and the receptor reduced the amount of Compound No. 11 in the receptor after 10 seconds to 2%. This increased to only 4% after 30 seconds at 135° C. Reduction of the processing temperature to 115° C. results in even lower transfer of Compound No. 11. In the solvent coated case 9% of Compound No. 11 was found in the receptor after 10 seconds and this did not increase on increasing the processing time to 30 seconds. The laminated sample showed 10% diffusion after 10 seconds increasing to 11% after 30 seconds.

Sensitometry

The cyan Compound No. 11 was tested in monochrome strips and was found to be sufficiently reactive to give good $D_{max}$ in the receptor layer in both constructions containing a barrier layer and no barrier layer as reported in the following Table.

Sensitometry after 30 Seconds Processing

| | T (°C.) | | | |
|---|---|---|---|---|
| | 115 | | 135 | |
| | Full | Rec | Full | Rec |
| Dmin | 0.32 | 0.16 | 0.49 | 0.41 |
| Dmax | 2.14 | 1.38 | 1.95 | 2.13 |

Full=measured on full construction
Rec=measure after receptor had been peeled apart These results demonstrate that it is possible to reduce the mobility of leuco dyes within photothermographic systems by incorporation of these moieties into discrete tetrameric molecules. This reduction in mobility is achieved whilst maintaining adequate reactivity. In addition, it is possible to reduce the amount of diffusion of the tetrameric leuco dyes into the next photosensitive layer without reducing the density of dye in the receptor by use of a suitable barrier.

EXAMPLE 3

Preparation of 1-tosyloxyhex-5-yne 5-hexyn-1-ol (14 g), pyridine (20 ml) and dichloromethane (60 ml) were mixed and cooled to 0° C. Tosyl chloride (30 g:1.1 equivalent) was added portion wise over 20 minutes. After 5 hours at 0° C., the reaction was transferred to a separating funnel and washed with 2N HCl (2×50 ml) and saturated sodium bicarbonate (2×50 ml). These were back extracted with dichloromethane (1×25 ml) and the combined organic layers washed with water (1×50 ml). After drying (Na$_2$SO$_4$), the liquid was filtered off and the solvent evaporated to leave the product—33.4 g (93%)—of sufficient purity to be used for the next step.

Preparation of p-(5-hexynyl-1-oxy)benzoyl Basic Blue 3

1-tosyloxyhex-5-yne (5.41 g) and caesium carbonate (6.5 g) were mixed with dry acetone (20 ml). Compound S (6.7 g) was added followed by more dry acetone (20 ml). After 3 hours at reflux, the reaction was cooled to 0° C., the solid filtered off and washed with acetone. The solvent was reduced to 15 ml, some 40° to 60° C. petrol added and the mixture heated to reflux. After cooling, the solid was filtered off and dried. Yield—7.06 g (89%).

Preparation of Compound No. 13 p-(5-hexynyl-1-oxy)benzoyl Basic Blue 3 (0.4 g) was mixed with dry, degassed octane (25 ml). On heating to reflux the solid dissolved and a 10% solution of cobalt cyclopentadienyl dicarbonyl in heptane (0.2 ml) was added. After 4.5 hours reflux, the reaction was cooled on ice and the solution filtered off. The residual solid was washed with 40°

C. to 60° C. petrol, then purified by chromatography to give the product (0.24 g, 60%).

The structure was confirmed by $^1$H and $^{13}$C-NMR spectroscopy.

Preparation of 1-tosyloxyundec-10-yne 10-undecyn-1-ol (9.9 g) was dissolved in pyridine (8.25 ml) and dichloromethane (30 ml) before cooling to 0° C. Tosyl chloride (13.7 g:1.2 equivalents) was added portion-wise. When the addition was complete, the reaction was transferred to the fridge and left overnight. In the morning the solution was washed with 2N HCl (2×50 ml) and saturated sodium bicarbonate (2×75 ml). The aqueous phases were washed with dichloromethane (1×25 ml). The combined organic phases were dried (MgSO$_4$) before removing the solvent in vacuo. Yield—19 g (100%).

NMR spectroscopy showed slight contamination with residual tosyl chloride. The material was used without further purification.

Preparation of p-(10-Undecynyl-1-oxy)benzoyl Basic Blue 1-tosyloxyundec-10-yne (6.44 g), caesium carbonate (9.78 g) and Compound B (8.9 g) were mixed in dry acetone (50 ml). After 5.5 hours reflux, the reaction was cooled before filtering and washing the solid with acetone. Evaporation gave a mixture of the desired product and p-tosyloxybenzoyl Basic Blue 3. Chromatography on SiO$_2$ using Et$_2$O/60° to 80° C. petrol (3:7) gave the product 9.86 g (83%).

Preparation of Compound No. 14)

p-(10-undecynyl-1-oxy)benzoyl Basic Blue 3 (5 g) was dissolved in hot, dry, degassed, n-octane (200 ml). A 10% solution of cobalt cyclopentadienyl dicarbonyl in heptane (1 ml) was added and the whole refluxed for 24 hours. It was cooled and the solution filtered off. The residual solids were chromatrographed on SiO$_2$ using toluene/Et$_2$O (9:1). Some unreacted starting material came off first (more remained in the octane solution) followed by the product—2.67 g (53%).

The structure was confirmed by $^1$H and $^{13}$C NMR spectroscopy.

Preparation of Bis(2-tosyloxyethoxy)-2-butyne

Bis(2-hydroxyethoxy)-2-butyne (17.4 g) and pyridine (28 ml) were dissolved in dichloromethane (40 ml). After cooling to 0° C., tosyl chloride (42 g) in dichloromethane (80 ml) was added over 15 minutes. The reaction was left in the fridge over the weekend before working up by washing with 2N HCl (2×50 ml), saturated sodium bicarbonate solution (2×50 ml) and water (1×50 ml). After drying, evaporation gave a dark oil (38.6 g).

This could be purified by chromatography on SiO$_2$ using ether/40° to 60° C. petrol (9:1) to give a clear oil which solidified on standing.

Preparation of bis(2-[p oxybenzoyl Basic Blue] ethoxy)-2-butyne

Bis(2-tosyloxyethoxy) 2-butyne (4.52 g), caesium carbonate (9.2 g) and Compound B (8.34 g) were dissolved in dry acetone (50 ml). After 5 hours at reflux, it was cooled and the solid filtered off and washed with acetone. The crude product could be purified by chromatography on SiO$_2$ using Et$_2$O/40° to 60° C. petrol (4:1) then 100% Et$_2$O. Yield—4.43 g (46%).

A further 1.43 g (15%) contaminated with about 15% of the monotosyl compound was also collected.

Preparation of Compound No. 15

Bis(2-[p-oxybenzoyl Basic Blue 3]-ethoxy)-2-butyne (2 g) was dissolved in hot, dry, degassed octane (100 ml) with stirring. 10% cobalt cyclopentadienyl dicarbonyl in heptane (1 ml) was added and the reaction refluxed for 7 hours. It was then filtered hot and the residual oil washed with 60° to 80° C. petrol. The product was isolated by chromatography on SiO$_2$. Using 100% Et$_2$O removed unreacted starting material while the product came off using acetone/Et$_2$O (1:1). Yield—1.12 g (56%). The $^1$H and $^{13}$C NMR spectra were consistent with the assigned structure.

Diffusion Studies

A silver soap was prepared from 11% ethanol half-soap homogenate (200 g), ethanol (228 g) and 10% Butvat B-72 in ethanol (40 g). This was halidised with HgBr$_2$ in ethanol (0.72g/20 ml) (3.8 ml) for 1 hour followed by ZnBr$_2$ in ethanol (0.45 g/20 ml) (3.8 ml) for 2 hours. Solid Butvar B-72 (25.4 g) was then added, followed by FC431 (fluorinated surfactant) (0.75 g) and stirring continued for a final 2 hours.

Silver soap (10 g) was sensitised with Dye (1) (0.04% in MeOH) (1 ml). A solution of 4-methylphthalic acid (0.025 g) in ethanol (1 ml) was added, followed by Compound No. 14 (0.13 g) and toluene (2 ml). The emulsion was coated at 75 µm wet thickness onto opaque polyester base previously coated with 15% VYNS in methyl ethyl ketone/toluene which had been dried for 6 minutes at 70° C.

All operations were carried out under red safelight conditions.

The other Compounds tested and the quantities used are reported in the following Table.

TABLE 1

| Compound | Soap wt. | Leuco wt. | Acid wt. | Sensitiser | Sensitiser volume of 0.04% solution | Toluene |
|---|---|---|---|---|---|---|
| C | 10 g | 0.10 g | 0.15 g | Dye (1) | 0.5 ml | 1 ml |
| 1 | 10 g | 0.104 g | 0.15 g | Dye (1) | 0.5 ml | 1 ml |
| 13 | 15 g | 0.10 g | 0.10 g | Dye (2) | 1 ml | 3 ml |
| 15 | 10 g | 0.112 g | 0.10 g | Dye (2) | 1 ml | 3 ml |

Samples were heated on a hot block at 115° C. or 135° C. for varying lengths of time. The coatings were chopped into 1 inch square pieces and half were dissolved in a fixed volume of methyl ethyl ketone before oxidising with NBS. The visible spectrum was run on the samples (diluted if necessary) before and after the oxidation. The soap layer was removed from the other samples and the procedure repeated on the VYNS receptor layer. These figures allow the percentage leuco remaining in the soap layer to be calculated as a function of processing temperature and time. These figures are given in the following Tables.

TABLE (processed at 115° C.)

| Processing Time (secs) | Monomer C | Dimer 1 | Trimer 13 | Trimer 14 | Hexamer 15 |
|---|---|---|---|---|---|
| 1 | 92.5 | — | 95 | 98 | 94 |
| 5 | 86 | 83 | 92 | 91 | 92 |
| 10 | 80 | 79 | 89 | 87 | 88 |
| 20 | 74 | 76 | 84 | 85 | 84 |
| 30 | 69 | 74 | 82 | 81 | 79 |

TABLE (processed at 135° C.)

| Processing Time (secs) | Monomer C | Dimer 1 | Trimer 13 | Trimer 14 | Hexamer 15 |
|---|---|---|---|---|---|
| 1 | — | 81 | 90 | — | 91 |
| 2 | 75 | 75 | 85 | — | 89 |
| 5 | 62* | 68 | 77 | 82 | 85 |
| 10 | 56 | 60 | 71 | 76 | 78 |
| 20 | 49 | — | — | 71 | — |

* = for 6 seconds

From these figures it can be seen that increasing the number of leuco moieties per molecule reduces the leuco mobility, more noticeably at higher processing temperatures.

Sensitometry

The coatings outlined above were imaged on an EG&G sensitometer equipped with a Wratten filter No. 47B (for Dye (1) sensitisation) or No. 58 (for Dye (2) sensitisation). The image was a 0 to 3 wedge with $10^{-3}$ seconds exposure. The resultant latent images were developed by heating at 135° C. for 15 seconds. The silver layer was removed and a scanning densitometer used to measure the image quality in the receptor layer. The results are given in the following Table.

| Compound | Dmax | Dmin | SP-1 | Con-1 |
|---|---|---|---|---|
| C | 2.98 | 0.38 | −2.12 | 2.54 |
| 1 | 3.19 | 0.56 | −2.01 | 3.04 |
| 13 | 2.26 | 0.30 | −2.11 | 1.43 |
| 14 | 1.33 | 0.15 | −2.53 | 1.04 |
| 15 | 1.37 | 0.90 | −3.28 | 1.58 |

These unoptimised formulations gave reasonable images with the leuco dyes despite their size and reduced mobility.

EXAMPLE 4

Preparation of 4-Armed Star Molecule (Stage (1))

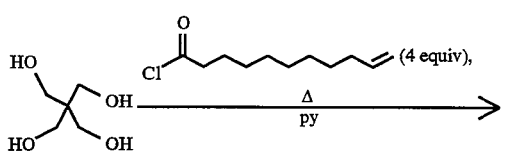

-continued
(Stage (1))

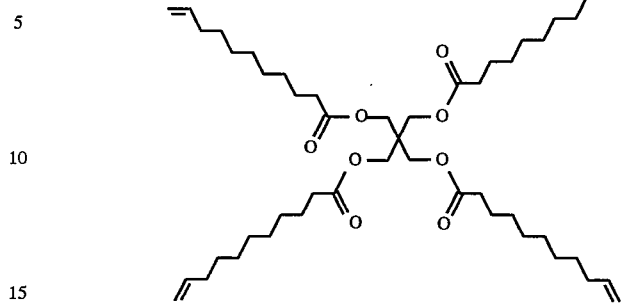

A stirred suspension of pentaerythritol (3.40 g, 0.025 mol) in pyridine (freshly distilled from KOH; 40 ml) was warmed to 45° to 50° C. to solution. With the apparatus connected to a supply of nitrogen, 10-undecenoyl chloride (21.29 g, 5% excess) was added dropwise over 20 minutes. A thick precipitate formed as the reagents mixed. the mixture was stirred vigorously at 45° to 50° C. for a further 2 hours, then allowed to cool.

Water (50 ml) was added carefully, followed by ether (50 ml). The ethereal phase was separated, washed successively with 10% hydrochloric acid (3×30 ml), and saturated aqueous sodium bicarbonate (50 ml), dried (MgSO$_4$), and evaporated to give an oil (18.77 g).

The crude product (5.01 g) was separated by flash chromatography on silica 60 (40 to 63µ) using 15% ether in petrol as eluant to give the pure tetra-alkene as a colourless oil (2.93 g, 55%).

Stage (2)

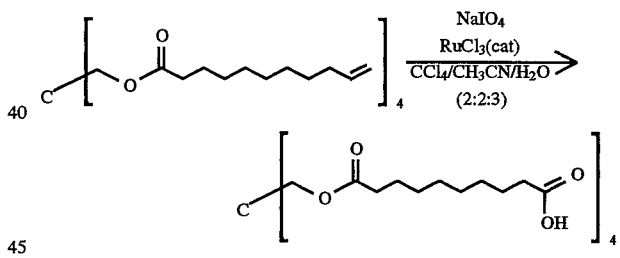

A 500 ml round-bottomed flask was charged with a "rugby-ball" magnetic stirrer, carbon tetrachloride (24 ml), acetonitrile (24 ml), water (36 ml), tetra-alkene (2.40 g, 3.0 mmol), and sodium periodate (10.52 g, 0.049 mol). To this biphasic solution, ruthenium trichloride 957 mg, 2.3 mol %) was added, and the entire mixture was stirred vigorously at room temperature for 42 hours.

CH$_2$Cl$_2$ (120 ml) was added to the mixture, which was then filtered under suction to remove the precipitate. The precipitate was washed well with CH$_2$Cl$_2$. The aqueous layer was separated from the combined filtrates, and extracted with CH$_2$Cl$_2$ (3×50 ml). The combined extracts were then dried (Na$_2$SO$_4$). A dark oil separated to the top of the CH$_2$Cl$_2$ on drying. The whole was evaporated to give an off-white solid (2.59 g), which was taken up into CH$_2$Cl$_2$ (50 ml). The biphasic solution was transferred to a separating funnel; the dark oil was separated, and washed with CH$_2$Cl$_2$ (2×10 ml). Solvent evaporation of the dark oil gave a solid (2.49 g).

$^1$H NMR analysis of this crude product in d$_6$-DMSO showed conversion to the tetracid to be incomplete, in that a CHO absorption was evident at δ8.3.

The reaction was therefore continued with the amounts of reagents as follows:

crude product (2.43 g), CCl$_4$ (2 µml), CH$_3$CN (24 ml), water (36 ml), sodium periodate (10.52 g), and ruthenium trichloride (57 mg). The mixture was stirred vigorously at room temperature for a further 2 days, then worked up as before to give the tetracid as a solid (0.78 g).

The tetracid may readily be reacted with a functionalised leuco dye in a similar manner to Example 1 to yield a tetrameric dye releaser.

EXAMPLE 5

Compounds Having Polymeric Backbones

POLYMER CHARACTERISATION

Differential Scanning Calorimeter

The glass transition temperature was measured using a Du Pont DSC 2100 analyser at a rate of 10° C./min, following a controlled cool at 10° C./min. The temperature quoted was taken from the maximum point of inflexion.

Molecular Weight Analysis; Gel Permeation Chromatography

Calibration of the instrument was carried out using polystyrene standards, with tetrahydrofuran as the solvent in all cases.

In the case of polymeric materials, a compound number has been assigned to the generalised polymeric structure. Molecular weight (Mw) information is indicated by additional numbers. For example, Compound No. 18/14 is indicative of a polymer prepared from methacrylate leuco monomer and butyl methacrylate monomer with the molecular weight of the resulting copolymer being between 14,000 and 14,999. Additional detail, such as the weight percentage of leuco monomer contained in the polymer is reported separately for each sample.

i) Preparation of the Protected Leucos

A) Preparation of 3,7-Bis(N,N-diethylamino)-10-(4'-(8"hydroxyoct-1"-yloxy) benzoyl)phenoxazine (Compound Compound B (25.7 g, 58 mmol), 8-iodooctan-1-ol (14.78 g, 58 mmol) and caesium carbonate (22.8 g, 70 mmol) were heated at reflux in dry tetrahydrofuran (100 ml) for 5 hours. The mixture was cooled to room temperature, filtered and the filtrate was evaporated. The residue was taken up into ether (200 ml) and the solution was washed with water (200 ml). The organics were dried (MgSO$_4$), filtered and evaporated to give the desired ether (31.96 g, 93%) as a thick yellow gum which was used without further purification.

B) Preparation of 3,7-bis(N,N-diethylamino)-10-(4'-(11"-hydroxyundec-1"-yloxy)benzoyl)phenoxazine (Compound H)

The ether was prepared as above from compound B (14.4 g, 32.5 mmol) and 11-bromoundecan-1-ol (8.16 g, 32.5 mmol) to give the ether (18.5 g, 94%) as a dark yellow gum which was used without further purification.

ii) Preparation of the (Meth)Acrylates.

A) Preparation of the acrylate of compound G.

A solution of compound G (5.9 g, 10.3 mmol) and dry triethylamine (1.14 g, 11 mmol) in dry dichloromethane (30 ml) was cooled to –25° C. and acryloyl chloride (1 g, 11 mmol) in dry dichloromethane (5 ml) was added over 15 minutes whilst keeping the temperature below –20° C. The mixture was stirred at room temperature for 1.5 hours. Tlc (1:1 ethyl acetate:petrol, silica) showed very little starting material. Water (20 ml) was added and the organics were separated, dried, filtered and evaporated to give the crude product as a green gum (5.9 g). This was chromatographed over silica gel 60 in ethyl acetate/40–60 petroleum ether (1:1) to give the acrylate (2.8 g, 43%) as a yellow gum.

B) Preparation of the methacrylate of compound G.

A solution of Compound G (10.8 g, 18.8 mmol) and dry triethylamine (2.1 g, 19.5 mmol) in dry dichloromethane (50 ml) was cooled to –10° C. Methacryloyl chloride (2 g, 19 mmol) in dichloromethane (10 ml) was added over 15 minutes and the mixture stirred at room temperature for 1 hour. Tlc (ethyl acetate/petroleum ether, 1:1) showed appreciable starting material remained. The reaction was recooled to –10° C. and triethylamine (1 ml) and methacryloyl chloride (0.5 ml) was added and the mixture stirred at room temperature for a further hour. Tlc showed that the reaction had gone. Water (7.5 ml) was added and the organics were separated, dried (MgSO$_4$), filtered and evaporated to give the crude product as a dark oil (13.6 g). Chromatography over silica gel 60 in ethyl acetate/40–60 petroleum ether (1:1) gave the methacrylate as a yellow gum (10.9 g, 91%).

iii) Preparation of the Styrenes

A) Preparation of the bromide (Compound I)

11.9 g (0.1 mol) of 4-aminostyrene was added to a solution of 15.9 g of sodium carbonate dissolved in 100 ml of water. 28.3 g (0.1 mol) of 11-bromoundecanoyl chloride was added to the aqueous mixture over 10 minutes with vigorous stirring, and with cooling to keep the temperature at about 30° C. The mixture was stirred for a further 5 minutes. The crude product was filtered off using a cotton filter pad. The product was stirred in about 500 ml of water which was acidified to pH 3–4 with hydrochloric acid. After stirring for 5 minutes the product was filtered off using a cotton filter pad, washed well with water and dried in air, and then under vacuum at 50° C. for 5 hours.

Yield=32.2 g (88%).

M.p. 92°–93° C.

B) Preparation of the styrene leuco.

A mixture of 4.45 g (0.01 mol) of compound B, 3.66 g (0.01 mol) of compound I and 4 g of caesium carbonate in 70 ml of anhydrous THF was refluxed with stirring for 21 hours. Thin layer chromatography (Tlc) (silica, ethyl acetate/petroleum ether 1:1) showed product with very little Compound B remaining. The product was isolated by column chromatography on silica using ethyl acetate/petroleum ether mixtures.

Yield: 4.1 g (56%)

M.p. 112°–114° C.

iv) Preparation of Polystyrene and Poly(meth) acrylate Leucos (Compounds 16 to 26)

The following method is a general description for the preparation of copolymers containing 33% weight leuco monomer; the quantities in parenthesis are those required for 50% weight leuco monomer.

2.0 g (4.0 g) of leuco monomer and 4.0 g of methacrylate comonomer were placed in a 50 ml Schott Duran screw top bottle. 24 ml (32 ml) of methyl ethyl ketone was added followed by 0.180 g (0.24 g) of AIBN and 90 microliters (120 microliters) of butanethiol. The mixture was flushed well with nitrogen and the bottle was sealed. The polymerisation bottle was placed in a water bath at 65° C. for 20 hours. The copolymer was isolated and purified by precipitation from ethanol. At least two precipitations were required to remove free leuco monomer. The yields of copolymers were usually less than 50%. This procedure gave polymers of about Mw—10,000, according to GPC.

v) Preparation of the Polyurethanes

A) Preparation of 1-bromo-10,11-dihydroxyundecane (compound J)

Trifluoroacetic anhydride (27.52 g, 0.139 moles) and hydrogen peroxide 30% (11.83 g, 0.348 moles) in dichloromethane (120 mls), were added to a stirred solution of 1-bromoundec-10-ene (24.50 g, 0.105 moles) and triethylammonium trifluoroacetate (11.38 g, 0.053 moles) in dichloromethane (125 mls). Stirring was continued for one hour after the addition was complete, after which time the solvent was evaporated. The residue was taken up into ether and washed with water and 2M sodium carbonate. The organics were then dried ($MgSO_4$), filtered and evaporated. The solid was then triturated with 40–60 petrol and filtered to give the product as a white solid. (5.3 g, 20%).

B) Preparation of the polyurethane of 1,6-diisocyanatohexane and 1-bromo-10,11-dihydroxyundecane (Compound K)

Under a blanket of argon, 4 (2.18 g, 8.2 mmol), 1,6-diisocyanatohexane (1.51 g, 9 mmol) and the catalytic amount of DBTDL were heated at reflux in dry methyl ethyl ketone (10 ml) for 35 minutes. The solution was allowed to cool for 30 minutes before being poured into stirred methanol (ca. 50 ml). The methanol was removed by evaporation to give a gum which was dried overnight in vacuo at 50° C. and used without further purification. Selected signals in the $^{13}C$ nmr spectrum were used to confirm that the desired prepolymer had been made.

Yield: 3 g, 59%.

C) Preparation of the polyurethane of diphenylmethane-4,4'-diisocyanate and 1-bromo-10,11-dihydroxyundecane (Compound L)

Under a blanket of argon, 4 (2.5 g, 9 mmol) and diphenylmethane-4,4'-diisocyanate (2.58 g, 10 mmol) were stirred at room temperature in dry methyl ethyl ketone (12 ml) for one hour. Following the addition of a catalytic amount of DBTDL, the mixture was heated at reflux for forty minutes. The solution was allowed to cool for 30 minutes before being poured into stirred methanol (ca. 50 ml). The gum was isolated, dried overnight in vacuo at 50° C. and used without further purification.

Yield: 3.6 g, 74%.

D) Attachment of the Leuco Dye to Compound L (Compound 27)

Compound B (2.58 g, 5.8 mmol), Compound L (3 g, 5.8 mmmol) and caesium carbonate (2.26 g, 6.9 mmol) were heated at reflux in dry tetrahydrofuran (30 ml) over night. The mixture was cooled to room temperature, filtered and the filtrate evaporated. The residue was taken up into methyl ethyl ketone (100 ml) and washed with water (100 ml). The organics were dried ($MgSO_4$), filtered and solvent volume reduced. This was then placed on a silica plug and washed with copious amounts of ether. The product was removed from the plug with methyl ethyl ketone, evaporated and dried overnight at 50° C. in vacuo. Compound K was reacted in the same way to give Compound 28.

Yield: 3.2 g, 63% vi) Preparation of Polysiloxanes

A) Fractionation of Commercially Available Polysiloxane

Dow 1107 (75 g) was dissolved in toluene (150 ml) and cooled in a fridge. It was then added to methanol (600 ml) and shaken vigorously. After settling, the lower layer was run off and dissolved in toluene (100 ml). This was added to methanol (500 ml) and the lower layer again collected after shaking and separation. Residual solvent was removed in vacuo to leave 45 g of a clear oil.

B) Attachment of Bromoalkyl Side Chains

Purified Dow 1107 (6.0 g) and undecenyl bromide (7.78 g) were dissolved in toluene (90 ml). The solution was bubbled with nitrogen for thirty to sixty minutes. Platinum catalyst Petrarch PC072 (platinum divinyl tetramethyl disiloxane in xylene, 200 microliters) was added. The reaction was placed in an oil bath at 80 to 90° C. and heated under an inert atmosphere for 7 hours. The temperature was reduced to 50° to 60° C. and hex-1-ene (30 milliliters) was added followed by further platinum catalyst (100 microliters). Heating was maintained for 15 hours. The reaction was removed from the oil bath and charcoal was added. After stirring for twenty minutes, this was filtered through Hyflo and evaporated to near dryness. The residual oil was poured into methanol (100 ml) in a separating funnel with the residues being washed in with toluene (20 ml). After vigorous shaking, the oil which separated was run off and residual solvent removed in vacuo.

Yield=16.6 g

The $^1H$ nmr spectrum showed a 2:1 ratio of hexyl to bromoundecyl side chains.

This procedure was used to prepare C-19, C-10 (as the tosylate) and C-4 analogues. In addition, an analogue was prepared with undecenyl bromide but using styrene instead of hex-1-ene.

C) Attachment of Leuco to Siloxane Polymer (Compound 33)

Modified polysiloxane (with 11-bromoundecyl and styryl side chains in the ratio 45:55) (5.93 g, 1.1 equivalents), Compound B (4.45 g, 1 equivalent) and caesium carbonate (4.89 g, 1.5 equivalents) were suspended in anhydrous THF (40 ml) and heated at reflux under nitrogen for 17 hours. After cooling to ambient temperature, the solution was filtered through silica gel with the gel being washed with further THF to remove most of the product. The bulk of the THF was evaporated off and the residue poured into methanol (150 ml). The supernatant was decanted and the residual oil dissolved in toluene (20 ml). Methanol (150 ml) was added to reprecipitate the product. The procedure was repeated and the yellow oil dried in vacuo. Further product was recovered from the combined supernatant liquors on standing.

Yield=3.69 g.

The $^1H$ nmr spectrum indicated approximately 55% styryl, 35% undecyl leuco and 10% undecyl bromide.

Compounds 29 to 32 and 34 were prepared similarly. In the case of the C-10 side chain the leuco was reacted with the tosylate. Residual tosyl groups were later exchanged for bromo using excess anhydrous lithium bromide in THF.

FORMULATION

The polymeric leucos described in this Example have been tested using a formulation based on one of the three formulas given below. Generally, the poly(meth) acrylate and polystyrene leucos were tested using formulations based on Type 1 and 2, with the polyurethane and polysiloxane leucos being tested using formulations based on Type 3. Formulations have not been optimised for any particular polymeric leuco.

i) Type 1 Formulation

| | |
|---|---|
| Halidised soap | 5 g |
| Dye (3) (0.01% EtOH) | 0.075 ml |
| Test Compound | 0.15 g |
| 4-MPA (methyl phthalic acid) | 0.05 g |
| Acetone | 1.5 ml |
| FC431 | 0.05 g |

Coat on VYNS receptor at 75 μm wet thickness.

Halidisation of Soap

| | | Mixing time (minutes) |
|---|---|---|
| Acetone | 60 g | |
| Butvar B72 (10% w/w IPA isopropyl alcohol) | 40 g | 10 |
| 1/2 soap (11% in Ethanol) | 55 g | 20 |
| HgBr2 (0.72 g/5 ml MeOH) | 0.375 ml | 60 |
| ZnBr2 (0.45 g/5 ml MeOH) | 0.625 ml | 120 |
| Butvar B72 (10% w/w/IPA) | 130 g | 60 | ii) Type 2 Formulation

| | |
|---|---|
| Halidised Soap | 5 g |
| Dye (3) (0.01% EtOH) | 0.075 ml |
| Test Compound | 0.15 g |
| 4-MPA | 0.05 g |
| MEK | 1.5 ml |
| FC431 | 0.05 g |

Coat on VYNS receptor at 75 μm wet thickness.

Halidisation of Soap

| | | Mixing time (minutes) |
|---|---|---|
| MEK | 100 g | |
| VROH | 4 g | 20 |
| 1/2 soap (11% in Toluene) | 55 g | 20 |
| HgBr2 (0.72/5 ml MeOH) | 0.375 ml | 60 |
| CaBr$_2$.2H$_2$O (0.47 g/5 ml MeOH) | 0.625 ml | 120 |
| Butvar B72 (10% w/w/IPA) | 130 g | 60 | iii) Type 3 Formulation

| | |
|---|---|
| Halidised Soap | 5.0 g |
| Dye (1) 0.04%) | 0.50 ml |
| 4MPA | 0.050 g |
| EtOH | 0.50 ml |
| Test Compound | 0.150 g |
| Toluene | 2.0 ml |

Coated on a VYNS receptor at 75 μm wet thickness, with an interlayer of PVAL (2% MeOH) coated at 25 μm wet thickness.

Halidisation of Soap

| | | Mixing Time (minutes) |
|---|---|---|
| EtOH | 228 g | |
| Homogenate (11% in EtOH w/w) | 100 g | |
| B72 solution (10% in EtOH w/w) | 40 g | 15 |
| HgBr2 (0.036 g/ml MeOH) | 3.8 ml | 60 |
| ZnBr2 (0.0225 g/ml MeOH) | 3.8 ml | 120 |
| B72 | 25.4 g | 120 |
| FC 431/EtOH | 0.75 g/2.0 g | 15 |

Sensitometric data are given for the total construction, developed at 135° C. unless otherwise stated.

A) Polysiloxanes

Polysiloxane leucos were shown to develop in Dry silver formulations as reported in the following Table.

| Compound No. | Mw | Tg | Dmax | Dmin | Time (seconds) |
|---|---|---|---|---|---|
| 33-A | 3000 | +12° C. | 1.36 | 0.16 | 10 |
| 33-B | 14100 | +24° C. | 2.03 | 0.88 | 10 |
| 30 | 10400 | −2° C. | 0.33 | 0.10 | 10 |
| 30* | 10400 | −2° C. | 1.82 | 0.33 | 10 |

For Compound 33, A and B denote different fractions obtained during the purification process. The latter result for the polysiloxane 30, highlighted by an asterisk, is for the polymer tested in a formulation containing twice the original quantity of 4-MPA.

B) Poly(meth) acrylates and Polystyrenes

The homoacrylate Compound 16 was tested and found to develop in Dry Silver, although contrast was not good.

| Compound No. | Mw | DSC | Dmax | Dmin | Time (seconds) |
|---|---|---|---|---|---|
| 16/14 | 14,300 | Tm-85° C. (3.92 J/g) | 0.82 | 0.39 | 40 |

Consequently, copolymers with methyl acrylate were prepared in an attempt to prepare an amorphous polymer with a Tg significantly lower than the development temperature of 135° C. Copolymers 17/54 and 17/14 both contain 33% by weight of the leuco monomer.

| Compound No. | Mw | Tg (°C.) | Dmax | Dmin | Time (seconds) |
|---|---|---|---|---|---|
| 17/54 | 54,500 | 31 | 1.49 | 0.63 | 20 |
| 17/14 | 14,300 | 24 | 1.73 | 0.25 | 5 |

The copolymers show an increased reactivity when compared to the homopolymeric leuco 16/14. In particular copolymer 17/14, with a combination of lower molecular weight and a glass transition temperature of 24° C., displays good reactivity. The following results are for polystyrene leucos with molecular weights(Mw) between 10,000 and 20,000. These polymers contained 50% by weight leuco monomer.

| Compound No. | Comonomer | Mw | Tg (°C.) | Dmax | Dmin | Time (secs.) |
|---|---|---|---|---|---|---|
| 25/11 | butyl methacrylate | 11,000 | 55 | 2.03 | 0.34 | 10 |
| 25/16 | butyl methacrylate | 16,300 | 55 | 1.18 | 0.20 | 10 |
| 25/19 | butyl methacrylate | 19,000 | 55 | 1.08 | 0.23 | 10 |

Reactivity decreased with increasing molecular weight. The effect of glass transition temperature (Tg) is shown in the following results. The polymethacrylate leucos in the following Table contain 33% by weight leuco monomer.

| Compound No. | Comonomer | Mw | Tg (°C.) | Dmax | Time (seconds) |
|---|---|---|---|---|---|
| 18/14 | butyl methacrylate | 14,000 | 40 | 1.89 | 10 |
| 20/11 | methyl methacrylate | 11,900 | 99 | 0.72 | 10 |
| 18/18 | butyl methacrylate | 18,500 | 45 | 1.93 | 20 |
| 19/20 | ethyl methacrylate | 20,900 | 67.5 | 1.32 | 20 |
| 20/18 | methyl methacrylate | 18,500 | 105 | 0.90 | 20 |

It is clear from the results shown in the above Table that reactivity decreases with increasing Tg. This result is also confirmed by the results for the polymethacrylate leucos shown in the following Table (in this case a Cll spacer group was used), and the polystyrene leuco examples in the subsequent Tables.

| Compound No. | Comonomer | Mw | Tg (°C.) | Dmax | Dmin | Time (secs.) | % leuco monomer content by weight |
|---|---|---|---|---|---|---|---|
| 21/11 | butyl methacrylate | 11,600 | 34 | 2.19 | 0.55 | 10 | 33 |
| 23/12 | ethyl methacrylate | 12,600 | 70 | 1.62 | 0.23 | 10 | 33 |
| 22/10 | butyl methacrylate | 10,500 | 45 | 2.18 | 0.38 | 10 | 50 |
| 25/11 | butyl methacrylate | 11,000 | 55 | 2.03 | 0.34 | 10 | 50 |
| 26/10 | styrene | 10,700 | 102 | 0.89 | 0.25 | 10 | 33 |

C) Polyurethanes

The polymeric leucos Compound No. 27 series contain by weight leuco and the compound No. 28 series 55%. Preliminary reactivity testing of these polymeric leucos showed that images were obtained. Comparing similar molecular weights, the compound No. 28 series generally displayed high reactivity when compared in identical formulations to the Compound No. 27 series. This is in keeping with the higher glass transition temperatures measured for the Compound No. 27 series, an example of which is shown in the following Table. Difficulties in peeling the polyurethane containing layer from the VYNS receptor layer were overcome by the use of a polyvinyl acetal interlayer (0.5 micron).

| Compound No. | Mw | Mw/Mn | Tg (°C.) | Dmax | Dmin | Time (seconds) |
|---|---|---|---|---|---|---|
| 28/15 | 15,600 | 2.01 | 61 | 1.94 | 0.59 | 5 |
| 27/10 | 10,300 | 1.54 | 104 | 0.69 | 0.23 | 5 |

The following Table shows a fall in reactivity with increasing molecular weight for the more reactive Compound No. 28 series.

| Compound No. | Mw | Dmax | Dmin | T (seconds) |
|---|---|---|---|---|
| 28/2 | 2,200 | 2.06 | 0.30 | 2 |
| 28/6 | 6,460 | 1.43 | 0.55 | 2 |
| 28/15 | 15,600 | 1.30 | 0.30 | 2 |

D) Variation of Reactivity with Formulation

The polymethacrylate Compound No. 22/10 was tested in different formulations.

| Compound No. | Formulation | Mw | Dmax | Dmin | Time (seconds) |
|---|---|---|---|---|---|
| 22/10 | 1 | 10,500 | 2.01 | 0.23 | 10 |
|  | 2 | " | 2.18 | 0.38 | 10 |
|  | 3 | " | 0.72 | 0.12 | 10 |

It is clear that formulation can have a great effect on reactivity. Further support for this conclusion is provided by studies of the polystyrene leuco Compound 26/10 which has been evaluated in Formulations 2 and 3.

| Compound No. | Formulation | Dmax | Dmin | Time (seconds) |
| --- | --- | --- | --- | --- |
| 26/10 | 2 | 0.89 | 0.25 | 10 |
|  |  | 1.51 | 0.34 | 20 |
|  |  | 1.78 | 0.46 | 30 |
|  | 3 | 1.75 | 0.20 | 10 |
|  |  | 1.95 | 0.30 | 20 |
|  |  | 1.92 | 0.38 | 30 |

None of the formulations have been optimised with respect to particular polymeric leucos. In addition to the formulation used for each colour forming layer, the polymers selected for use as interlayers (if they are found to be needed) and for the receptor layer, will all play a part in the final performance of the system. This can be seen by comparing data obtained for the total construction with that obtained for the receptor.

| Compound No. | Total Construction | | Receptor | | Time (seconds) |
| --- | --- | --- | --- | --- | --- |
|  | Dmax | Dmin | Dmax | Dmin |  |
| 22/10 | 2.01 | 0.23 | 1.37 | 0.18 | 10 |
|  | 1.99 | 0.32 | 2.25 | 0.26 | 20 |
|  | 1.88 | 0.45 | 2.29 | 0.38 | 30 |
| 26/10 | 1.75 | 0.20 | 0.97 | 0.14 | 10 |
|  | 1.95 | 0.30 | 1.52 | 0.23 | 20 |
|  | 1.92 | 0.38 | 1.71 | 0.30 | 30 |

Diffusion

Diffusion tests (carried out as described in Example 3) confirmed the polymeric compounds have significantly improved non-diffusing properties compared to the corresponding unballasted leuco dye.

Molecular weight (Mw) was clearly seen to influence the diffusion results. Three samples of Compound No. 25 polystyrene leucos were tested in both a solvent coated and a laminated construction and the results are shown in FIG. (1). The transfer of polymeric leuco out of the emulsion layer is significantly greater for the lowest molecular weight sample, Compound No. 25/11, with higher molecular weight samples Compound No. 25/16 and Compound No. 25/19 showing improved diffusion behaviour. Comparing the solvent coated construction with the laminated, it is seen that solvent greatly aids the transfer of polymeric leuco into the receptor during the coating stage. Comparison between the diffusion results for Compound No. 25/11 (FIG. (1b)) and Compound No. 26/10 (FIG. (2)) show that although both copolymers have similar molecular weights, Compound No. 26/10 shows much less diffusion. This can be explained by the higher Tg of 102° C. exhibited by Compound No. 26/10 compared with a Tg of 55° C. for Compound No. 25/11.

It has been common practice to place a polymeric interlayer between the standard VYNS receptor layer and the emulsion layer containing the polymeric leuco. The interlayer can enhance differential diffusion by retaining a small amount of the polymeric leuco, thereby preventing it from reaching the receptor. At the same time however, it may retain an amount of dye so reducing the final peeled apart Dmax. An improvement was obtained through the use of an interlayer, B72 with Compound No. 22/10 (FIG. (3)). The reactivity of this particular polymethacrylate leuco is such that an interlayer is a viable option to achieve superior differential diffusion.

Good diffusion results can also be obtained without an interlayer. Very similar diffusion results were obtained for a polystyrene leuco Compound No. 24/25 with and without an interlayer (FIG. (4)). The accompanying reactivity data for this polymer is rather slow, but this is believed to be at least partly due to the volume of toluene necessary to dissolve the sample.

| Compound No. | Mw | Tg (°C.) | Dmax | Dmin | Time (secs) |
| --- | --- | --- | --- | --- | --- |
| 24/25 | 25,300 | * | 1.57 | 0.19 | 5 |
|  |  |  | 1.86 | 0.24 | 10 |
|  |  |  | 2.03 | 0.33 | 15 |

Diffusion results for polysiloxane Compound No. 30/10 indicated approximately 5% of leuco is transferred during processing for 30 seconds at 135° C.

Polymeric leucos Compound Nos. 28/15 and 22/10 were tested under identical conditions so that a direct comparison could be made. It was found that leuco is transferred during the coating process, but that subsequent diffusion is of the same order in both cases and is less than 3% after 30 seconds.

EXAMPLE 6

Polymeric Leuco dyes

Preparation of Compound No. 35

To a 250 ml reaction flask equipped with mechanical stirrer, Dean-Stark trap fitted with a condenser closed with a drying tube filled with calcium sulphate (Drierite), and a thermometer fitted with a Therm-O-Watch sensor/controller were added 20 g of poly(ethylene glycol) (Carbowax 1000 from Union Carbide) and 125 g methyl ethyl ketone. A 26 gm portion of solvent was distilled out and collected in the Dean-Stark trap to remove moisture in the polyol. Heating was accomplished by two 250 watt infra-red lamps connected to the Therm-O-Watch controller. A solution of 25.92 g polyisocyanate (Desmodur N3300 from Miles having isocyanate equivalent weight 216) in 36 g methyl ethyl ketone was added followed by four drops of dibutyl tin dilaurate (Aldrich) and the solution was heated to 65° C. for six hours. Percent solids determined by loss on drying was 26.3%. Isocyanate equivalent weight of this solution determined by treatment of a weighed quantity with excess dibutyl amine in toluene solution and back titration with standard HCl solution after addition of isopropanol to the test solution was 2442 g/NCO equivalent. A 9.41 g portion of this solution (0.00385 equivalent NCO) was weighed into a clean flask. The hydroxy functional leuco dye, 3,7-bis (diethylamino)-10-(4-hydroxyethoxybenzoyl) phenoxazine (1.89 g, 0.00397 equivalent OH) dissolved in about 100 ml methyl ethyl ketone was added followed by four drops of dibutyl tin dilaurate catalyst and the mixture warmed to 70° C. for 1.5 hours. The infra-red spectrum of an aliquot of the resulting solution showed no isocyanate peak. Analysis by a thin layer chromatography on silica gel eluting with 75/25 v/v ethyl acetate/hexanes and development with iodine vapour showed no monomeric leuco dye remained. Evaporation of the solvent on a rotary evaporator gave the solid product, which shows a Tg of 0° C. by DSC.

Preparation of Compound No. 36

A 5.58 g portion of high molecular weight poly(ethylene glycol) (PEG 6000 from E. Merck Science having OH equivalent weight 3190) was dissolved in about 180 g methyl ethyl ketone and about 60 g of solvent was distilled into a Dean Stark trap to remove moisture. Polyisocyanate (1.0 g Desmodur N3300 from Bayer with NCO equivalent weight 192) was added in methyl ethyl ketone solution followed by one drop dibutyl tin dilaurate catalyst and the solution was heated to 65° C. for 2 hours. The infra-red spectrum showed NCO functionality remained. A solution of hydroxy functional leuco dye, 3,7-bis (diethylamino)-10-(4-hydroxyoctoxybenzoyl) phenoxazine (Compound G), 2.0 g equivalent OH, in 30 g methyl ethyl ketone was added and the solution held at 70° C. for 5 hours. The IR spectrum at this time showed no remaining NCO functionality. Thin layer chromatography showed a small amount of monomeric leuco dye remained in the sample. The solvent was removed on a rotary evaporator leaving solid polymeric leuco dye. DSC analysis showed Tg at −14° C.

Photothermographic Materials with Compound No. 35

The following were coated on ICI Type 994 PET film:

| First Trip: | 15% VYNS-3 in MEK/Toluene (50/50) coated at 62 μm wet and dried 4.5 minutes at 180° F. (82° C.) | |
|---|---|---|
| Second Trip: | Silver soap homogenate | 110.0 g |
| | Ethanol | 380.0 g |
| | HgBr$_2$ | 0.18 g |
| | Methanol | 10.0 ml |
| | Butvar B-72 | 26.0 g |
| | Fluorad FC431 | 1.00 g |
| | Ethanol | 10.0 ml |
| | coated at 75 μm wet and dried 4.5 minutes at 180° F. | |
| Third Trip: | 5% VROH in methoxypropanol coated at 75 μm wet and dried 4.5 minutes at 180° F. (82° C.) | |
| Fourth Trip: | Silver soap homogenate | 110.0 g |
| | Ethanol | 380.0 g |
| | HgBr$_2$ | 0.18 g |
| | Methanol | 10.0 ml |
| | Butvar B-72 | 26.00 g |
| | Fluorad FC431 | 1.00 g |
| | Ethanol | 10.0 ml |

To 12.5 g aliquots of the above the following were added:

| Sample A | Dye (3) (0.005 g/200 ml Toluene/Methanol 75/25) | 0.50 ml |
|---|---|---|
| | Compound E | 0.125 g |
| | Toluene | 3.00 ml |
| | 4-methylphthalic acid | 0.125 g |
| | Ethanol | 1.50 ml |
| Sample B | Dye (3) (0.005 g/200 ml Toluene/Methanol 75/25) | 0.50 ml |
| | Compound No. 35 | 0.75 g |
| | Toluene | 3.00 ml |
| | 4-methylphthalic acid | 0.125 g |
| | Ethanol | 1.50 ml |

A and B were coated 100μ wet and dried 4.5 minutes at 180° F.

Samples from each material were exposed to an E.G. & G Sensitometer for $10^{-3}$ seconds through 0 to 3 continuous density wedge and Wratten 25 red filter. The samples were then processed in a modified 3M model 9014 hot roll processor for 30 seconds at 280° F. (138° C.). Following the processing step, the layers above the image receiving layer were peeled away from the image receiving layer using Scotch 810 Magic Tape. A cyan image was observed to have transferred to the image receiving layer in the area corresponding to red light exposure. The following sensitometric data were obtained from the sample:

| Sample | Filter | Dmin | Dmax | Spd2 | TC2 | AC2 |
|---|---|---|---|---|---|---|
| A | R | 0.18 | 2.01 | 2.68 | 0.76 | 2.25 |
| B | R | 0.41 | 1.86 | 2.35 | 0.64 | 2.34 |

A test was then performed to determine the amount of leuco that diffused to the image receiving layer. A set of samples was processed without any exposure, after which the layers above the image receiving layer (hereafter referred to as 'donor') were peeled away from the image receiving layer (hereafter referred to as 'receptor'). 100.0 ml of 2-butanone were then added to jars containing the samples from trial 'A', which was observed to have dissolved the coated material. A 2.90 ml sample was removed from the solution of receptor to serve as a blank. To each of the donor- and receptor-containing jars a 1.00 ml aliquot of 0.100M N-bromosuccinimide was added, whereupon the colourless solution became a deep cyan colour. The donor and receptor samples were then diluted with 100 ml of 2-butanone. A similar procedure was used to prepare solutions of experimental trial 'B' except that only 10.0 ml was necessary to dissolve the receptor. The donor samples were diluted to 100.0 ml total volume.

A spectrophotometer was then used to measure the peak absorbance for each of the samples. On the basis of these numbers, the percentage of leuco that diffused to the receptor could be calculated based on the following formula:

$$\% \text{ leuco} = \frac{(\text{Receptor Absorbance})*(\text{dilution factor}) - (\text{Blank Absorbance})*(\text{dilution factor})}{(\text{Receptor Absorbance})*(\text{dilution factor}) + (\text{Donor Absorbance})*(\text{dilution factor})}$$

After 30 seconds processing time, experimental trial 'A' gave an average value of 12.2% of leuco diffused to the receptor, while trial 'B' gave a value of 0.15% of leuco diffused.

Light stability testing was conducted in an Atlas Ci35 Weatherometer using a xenon light source and no filters. Actual light stability data indicate a rise in Dmin of 0.67 for sample 'A' and no rise in Dmin for sample 'B', indicating that the level of polymeric leuco dye that diffuses to the receptor is extremely low.

Photothermographic Materials with Compound No. 36

The following were coated on ICI type 994 PET film coated with VYNS-3 at a coating weight of 0.500 g/ft$^2$ (5.4 g/m$^2$):

| First Trip: | Silver soap homogenate | 110.0 g |
|---|---|---|
| | Ethanol | 380.0 g |
| | HgBr$_2$ | 0.18 g |
| | Methanol | 10.0 ml |
| | Butvar B-72 | 26.00 g |
| | Fluorad FC431 | 1.00 g |
| | Ethanol | 10.0 ml |
| | coated at 75 μm wet and dried 4.5 minutes at 180° F. (82° C.) | |
| Second Trip: | 5% VROH in methoxypropanol coated at 75 μm wet and dried 4.5 minutes at 180° F. (82° C.) | |

| | -continued | |
|---|---|---|
| Third Trip: | Silver soap homogenate | 110.0 g |
| | Ethanol | 380.0 g |
| | HgBr$_2$ | 0.18 g |
| | Methanol | 10.0 ml |
| | Butvar B-72 | 26.00 g |
| | Fluorad FC431 | 1.00 g |
| | Ethanol | 10.0 ml |

To 25.09 of the above the following was added:

| C | Dye (3) (0.005 g/200 ml Toluene/Methanol 75/25) | 1.00 ml |
|---|---|---|
| | Compound E | 0.25 g |
| | Toluene | 3.00 ml |
| | 4-methylphthalic acid | 0.25 g |
| | Ethanol | 3.00 ml |
| D | Dye (3) (0.005 g/200 ml Toluene/Methanol 75/25) | 1.00 ml |
| | Compound No. 36 | 1.06 g |
| | Toluene | 3.00 ml |
| | 4-methylphthalic acid | 0.25 g |
| | Ethanol | 3.00 ml |

C and D were coated at 100 μm wet and dried 4.5 minutes at 180° F. (82° C.).

Samples from each material were exposed to an E.G. & G. Sensitometer for $10^{-3}$ seconds through a 0 to 3 continuous density wedge and Wratten 25 red filter. The samples were then processed in a modified 3M model 9014 hot roll processor for 30 seconds at 280° F. Following the processing step, the layers above the image receiving layer were peeled away from the image receiving layer using Scotch 810 Magic Tape. A cyan image was observed to have transferred to the image receiving layer in the area corresponding to red light exposure. The following sensitometric data were obtained from the sample:

| Sample | Filter | Dmin | Dmax | Spd2 | TC2 | AC2 |
|---|---|---|---|---|---|---|
| C | R | 0.17 | 1.95 | 2.45 | 0.99 | 2.86 |
| D | R | 0.35 | 1.94 | 2.44 | 0.88 | 2.66 |

A test was then performed to determine the amount of leuco that diffused to the image receiving layer. A set of samples was processed without any exposure, after which the layers above the image receiving layer (hereafter referred to as 'donor') were peeled away from the image receiving layer (hereafter referred to as 'receptor'). 10.0 ml of 2-butanone were then added to jars containing the samples from trials 'C' and 'D', which was observed to have dissolved the coated material. A 2.90 ml sample was removed from the solution of receptor to serve as a blank. To each of the donor- and receptor-containing jars a 1.00 ml aliquot of 0.100M N-bromosuccinimide was added, whereupon the colourless solution became a deep cyan colour. The donor samples were then diluted with 200 ml of 2-butanone.

A spectrophotometer was then used to measure the peak absorbance for each of the samples. On the basis of these numbers, the percentage of leuco that diffused to the receptor could be calculated based on the following formula:

$$\% \text{ leuco} = \frac{(\text{Receptor Absorbance})*(\text{dilution factor}) - (\text{Blank Absorbance})*(\text{dilution factor})}{(\text{Receptor Absorbance})*(\text{dilution factor}) + (\text{Donor Absorbance})*(\text{dilution factor})}$$

After 30 seconds processing time, experimental trial 'C' gave an average value of 11.4% of leuco diffused to the receptor, while trial 'D' gave a value of 4.1% of leuco diffused.

EXAMPLE 7

This Example demonstrates the use of a polymer bound leuco dye of a difference class, namely the "chromogenic" class disclosed in EP 0533008.

Preparation of Compound 37

An isocyanate functional polymer was prepared as described for the synthesis of Compound 35, resulting in a 30.2 wt % solution in MEK of polymer with an isocyanate equivalent weight of 2005. An aliquot of this solution (2.5 g, 12.5 meq isocyanate) was mixed with the hydroxyalkyl functional leuco dye B (0.838 g in 35 g MEK, 12.3 meq OH) and the mixture held at 65° C. for 2 hours. The infrared spectrum showed that all isocyanate had been consumed. The solvent was evaporated, leaving 1.7g polymer bound leuco dye developer.

Leuco dye B had the following structure, and was prepared by the methods disclosed in EP 0533008:

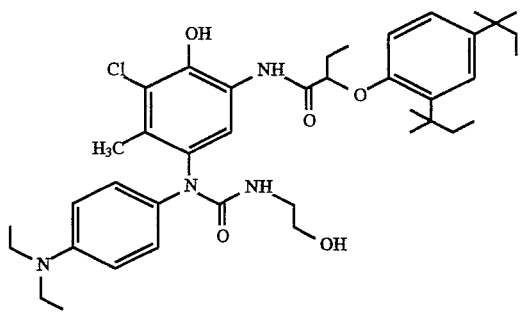

Evaluation in Photothermographic Media

A dispersion of silver behanate half soap was homogenised to 10% solids (90/10) in ethanol and toluene with 0.5% polyvinylbutyral (Butvat B-72). To 205 grams of the silver half soap dispersion was added 285 grams of ethanol. After 10 minutes of mixing, 6.0 ml of a mercuric bromide solution (0.36 g/20 ml methanol) was added. Then 8.0 ml of a zinc bromide solution (0.45 g/20 ml methanol was added 3 hours later. After 1 hour of mixing 26 grams of a polyvinylbutyral (Butvar B-72 available from Monsanto, St. Louis, Mo.) was added. To 40.1 grams of the prepared silver premix described above was added 2.5 ml of the sensitising dye (090 g/100 ml methanol) Dye (1). After 30 minutes the isocyanate ballasted (polymeric) leuco dye solution was added to a 8.43 gram aliquot of the sensitised silver premix. This leuco dye solution is described below:

| Component | Amount |
|---|---|
| Ballasted Leuco | $1.365 \times 10^{-4}$ moles of leuco dye present on polymer |
| Phthalazinone | 0.035 grams |

| Component | Amount |
| --- | --- |
| Tetrahydrofuran | 1.5 ml |
| FC 431 (fluorocarbon surfactant available from Minnesota Mining & Manufacturing Co., Saint Paul, Minnesota) | 0.075 ml |

A non-ballasted (monomeric) cyan colour forming leuco was also tested for comparison. The structure is shown below:

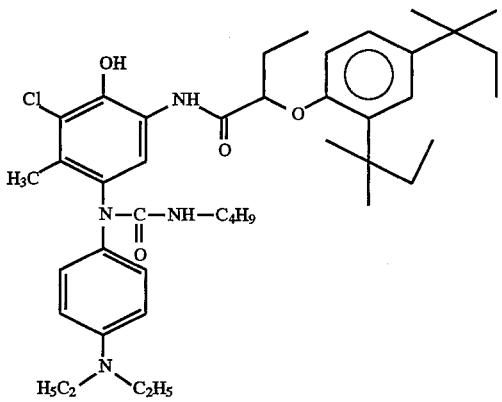

The silver leuco developer solutions were coated at 75 microns wet on a filled polyester base and dried for 5 minutes at 180° F. The samples were exposed using an EG and G sensitometer for $10^{-3}$ seconds with a xenon flash through a 47B Wratten filter and a 0 to 3 continuous wedge. The coatings were processed at 280° F. for 10 to 30 seconds using a heat blanket.

To study diffusion, a receptor and interlayer were coated onto a separate base. The receptor layer was prepared at a 15% VYNS (polyvinyl chloride-polyvinyl acetate) methyl ethyl ketone and toluene (50/50) solution. The interlayer was a 3% polyvinylbutral (Butvar B-72) in ethanol solution. The receptor was coated onto the base at a wet thickness of 75 microns and after drying the interlayer was coated at 50 microns. These were dried as described previously. Samples of the unexposed silver layer coating were laminated to the interlayer/receptor coatings using a 3M 1147 laminator set at 230° F. at a speed of 49 seconds per revolution. The base containing the silver layer was removed from the laminated silver/interlayer/receptor layers. This construction was tested for reactivity as described previously.

The diffusion of the non-ballasted cyan leuco and ballasted leuco were than tested by the following method. Unexposed samples were cut from each coating at each processing time in 1.5 inch×3.0 inch sections. Three samples were separated for replicates of the unoxidised samples versus three for the oxidised samples. The silver layers were carefully separated from the interlayers with Scotch tape, and the silver layers and interlayer/receptor layer base samples were placed in separate 2 oz. vials marked for either oxidation or no oxidation and for either receptor or donor (silver layer) samples. 5 mls of methyl ethyl ketone was added to each of the vials and shaken for 30 minutes. To those vials marked for oxidation 0.1 grams of lead dioxide was added and shaken for 30 minutes. The vials were left undisturbed for an additional 30 minutes and then a 1 ml aliquot was removed from the oxidised donor samples and diluted with an additional 4 mls of methyl ethyl ketone. The oxidised receptor samples, and unoxidised donor and receptor samples were not diluted further.

The absorption of these prepared samples using a UV/visible spectrometer was measured. Previous studies had shown a Beer's Law relationship for absorption of dye and concentration of unoxidised leuco within the coated layer using this sample preparation method. The percentage of unoxidised non-ballasted cyan leuco or ballasted unoxidised cyan leuco diffused to the receptor was calculated by the following method.

$$\frac{\text{(Absorbance of oxidised receptor layer} - \text{Absorbance of unoxidised receptor layer)}}{\text{(Absorbance of oxidised receptor layer} - \text{Absorbance of unoxidised receptor layer} + \text{(Absorbance of oxidised donor layer} - \text{Absorbance of unoxidised donor layer)}} \times 100$$

Results

The sensitometric results for the coated silver layers before and after lamination, and the percentage of unoxidised leuco transferred to the receptor are shown below.

| | Before Lamination | | | | |
| --- | --- | --- | --- | --- | --- |
| Sample | Dwell time | Dmin | Dmax | Speed 2 | Average Contrast |
| Unballasted Leuco | 10 sec. | 0.13 | 1.91 | 2.68 | 2.68 |
| | 20 sec. | 0.14 | 1.82 | 2.34 | 1.45 |
| | 25 sec. | 0.16 | 1.92 | 2.13 | 1.38 |
| Ballasted Leuco | 10 sec. | 0.11 | 0.95 | 3.30 | — |
| | 20 sec. | 0.12 | 1.52 | 2.91 | 1.58 |
| | 25 sec. | 0.14 | 1.65 | 2.77 | 1.52 |
| | 30 sec. | 0.14 | 1.62 | 2.48 | 1.26 |

| | After Lamination | | | | |
| --- | --- | --- | --- | --- | --- |
| Sample | Dwell time | Dmin | Dmax | Speed 2 | Average Contrast |
| Unballasted Leuco | 10 sec. | 0.12 | 1.37 | 3.03 | 1.51 |
| | 20 sec. | 0.13 | 1.79 | 2.81 | 2.17 |
| | 30 sec. | 0.14 | 1.71 | 2.48 | 1.74 |
| Ballasted Leuco | 20 sec. | 0.12 | 0.95 | 3.32 | — |
| | 30 sec. | 0.14 | 1.30 | 2.99 | — |

The ballasted leuco was reactive and formed the expected cyan image. The formation of the colour was slower than the unballasted leuco but the formulation was not optimised for this polymeric material.

| % Unoxidised Leuco Diffused To The Receptor | | |
| --- | --- | --- |
| Sample | 30 second dwell time | 45 second dwell time |
| Unballasted Leuco | 7–8 | 14 |
| Ballasted Leuco | 2–3 | 4.5–5.5 |

The polymeric leuco clearly gave decreased diffusion.

We claim:

1. A photothermographic element comprising a support bearing at least one photothermographic emulsion layer comprising:

(a) a photosensitive silver halide, (b) a non-photosensitive reducible silver source, (c) reducing agent for the non-photosensitive reducible silver source, and (d) an oleophilic polymeric binder, wherein said reducing agent comprises a compound comprising more than one leuco dye releasing moiety.

2. The photothermographic element according to claim 1 wherein said compound comprising more than one color leuco dye releasing moiety comprises leuco dye moieties attached via oxidisable groups whose oxidation causes release of the dye moiety, and said compound comprising more than one leuco dye releasing moiety is dissolved in said oleophilic binder.

3. The photothermographic element according to claim 1 wherein said compound comprising more than one leuco dye releasing moiety comprises dyes in their reduced leuco forms which are oxidised in the redox process, thus generating a desired dye, and said dyes are simultaneously cleaved from the rest of the molecule.

4. The photothermographic element according to claim 1 wherein said compound comprising more than one leuco dye releasing moiety has the general formula (I):

$$X-(-A-R^1-Y^1-D^1)_n \qquad (I)$$

wherein;

n is an integer of at least 2, each A is independently a member selected from the group consisting of a bond and divalent linking group, each $R^1$ independently represents a group capable of being oxidised by a silver salt, each $Y^1$ independently represents a divalent linking group capable of being oxidatively cleaved from $R^1$ and/or $D^1$, each $D^1$ independently represents a leuco dye moiety which forms a thermally diffusible dye on cleavage of a bond to $Y^1$, and X is a member selected from the group consisting of an atom and group to which each A is bonded.

5. The photothermographic element according to claim 4 wherein $Y^1$ is a group selected from the group consisting of

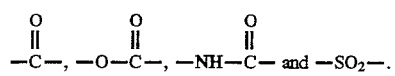

6. The photothermographic element according to claim 5 wherein $Y^1$ is —SO$_2$— and $R^1$ is an aryl amino group.

7. The photothermographic element according to claim 4 wherein;

$Y^1$ is a member selected from the group consisting of

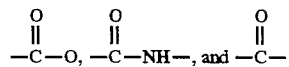

and $R^1$ is of the general formula (IV):

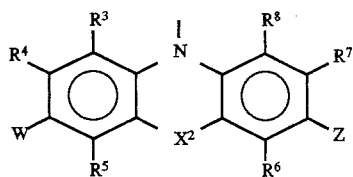

wherein;

$X^2$ is a member selected from the group consisting of S, O and N—R in which R is a member selected from the group consisting of an alkyl and aryl groups, $R^3$, $R^4$, $R^5$, $R^6$, $R^7$ and $R^8$ are each independently members selected from the group consisting of hydrogen, halogen and alkyl groups having from 1 to 4 carbon atoms, or $R^3$ together with $R^4$ and $R^7$ together with $R^8$ may independently represent atoms which are members selected from the group consisting of C, N, O and S to complete a fused ring system, W and Z are independently members selected from the group consisting of hydrogen, an alkyl group having from 1 to 4 carbon atoms, alkoxy and alkythio groups having from 1 to 4 carbon atoms, acyloxy, —OH, —SH, and a group represented by —NR$^9$R$^{10}$, where R$^9$ and R$^{10}$ are each independently members selected from the group consisting of hydrogen, an alkyl group, an aryl group, an aralkyl group, an acyl group and an aroyl group (provided that not both of R$^9$ and R$^{10}$ are hydrogen), or where R$^9$ and R$^{10}$ together represent the necessary atoms which are members selected from the group consisting of C,N,O and S to complete a 5-, 6-, or 7-membered heterocyclic ring group, or where one or both of R$^9$ and R$^{10}$, together with R$^4$, R$^5$, R$^6$ or R$^7$, represents the necessary atoms which are members selected from the group consisting of C,N,O and S to complete a 5- or 6-membered heterocyclic ring group fused to the phenyl ring on which the —NR$^9$R$^{10}$ group is attached;

with the proviso that one of W, $X^2$, Z and $R^3$ to $R^8$ has an unused valency to enable bonding to A.

8. The photothermographic element according to claim 1 wherein said compound comprising more than one leuco dye releasing moiety has the general formula (II);

$$X-(-A-Y^2-D^2)_n \qquad (II)$$

wherein;

X is independently a member selected from the group consisting of an atom and group to which each A is bonded, each A is independently a member selected from the group consisting of a bond and divalent linking group, n is an integer of at least 2, each $Y^2$ independently represents a divalent linking group capable of being oxidatively cleaved from $D^2$ and/or A, and each —$D^2$ independently represents a leuco dye moiety which forms a thermally diffusible dye on cleavage of a bond to $Y^2$.

9. The photothermographic element according to claim 8 wherein $D^2$ is derived from a member selected from the group consisting of bisphenol leuco dye, bisnaphthol leuco dye, phenolic leuco dye, indoaniline leuco dye, imidazole leuco dye, azine leuco dye, oxazine leuco dye, diazine leuco dye, thiazine leuco dye, aldazine leuco dye and ketazine leuco dye.

10. The photothermographic element according to claim 9 wherein $Y^2$ is a member selected from the group consisting of:

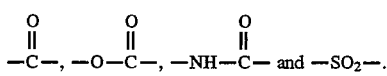

11. The photothermographic element according to claim 4 wherein A is a member selected from the group consisting of a hydrocarbon chain of at least 6 carbon atoms, a polyether chain and a polysiloxane chain with at least 6 chain atoms.

12. The photothermographic element according to claim 4 wherein;

X is a member selected from the group consisting of a carbon atom, an oxygen atom, a sulphur atom, a phosphorous atom, an aliphatic group, a ring and a polymer backbone.

13. The photothermographic element according to claim 12 wherein:

X is a member selected from the group consisting of aromatic, non-aromatic homocyclic and heterocyclic rings with ring atoms selected from C, N, O, S, Si and P.

14. The photothermographic element according to claim 13 wherein:

X is a member selected from the group consisting of a phenyl and cyclotetrasiloxane ring.

15. The photothermographic element according to claim 12 wherein:

X is a member selected from the group consisting of a polyacrylate, polymethacrylate, polystyrene, polyurethane, polysiloxane and a copolymer thereof.

16. The photothermographic element according to claim 1 wherein said compound comprising a plurality of leuco dye releasing moieties has the general formula:

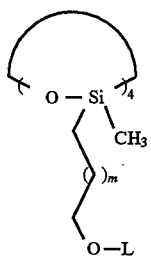

wherein;

m is an integer and

L is a leuco dye releasing moiety.

17. The photothermographic element according to claim 1 wherein said compound has the general formula:

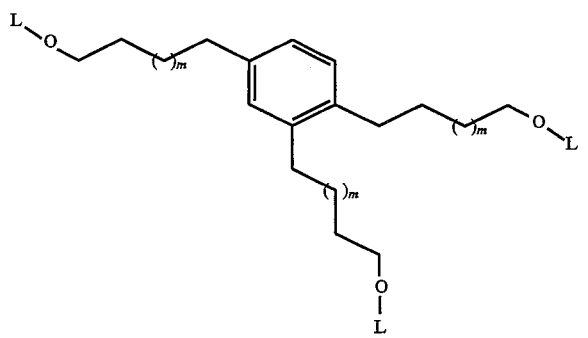

wherein;

m is an integer and

L is a leuco dye releasing moiety.

18. The photothermographic element according to claim 1 wherein said compound has the general formula:

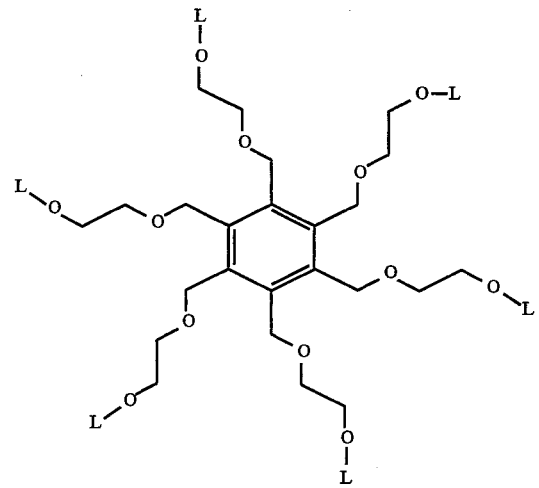

wherein;

L is a leuco dye releasing moiety.

19. The photothermographic element according to claim 1 wherein said compound has the general formula:

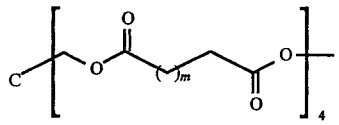

wherein;

m is an integer and

L is a leuco dye releasing moiety.

20. The photothermographic element according to claim 16 wherein;

L is

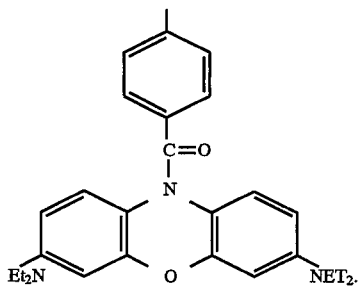

21. A photothermographic element comprising a support bearing at least one photothermographic emulsion layer comprising:

(a) a photosensitive silver halide, (b) a non-photosensitive reducible silver source, (c) reducing agent for the non-photosensitive reducible silver source, and (d) an oleophilic polymeric binder, wherein said reducing agent comprises a compound comprising more than two color leuco dye releasing moieties.

22. The photothermographic element of claim 21 in which said compound comprises 3 to 100 color leuco dye releasing moieties.

23. The photothermographic element according to claim 21 wherein said compound comprising more than two color leuco dye releasing moieties comprises leuco dye moieties attached via oxidisable groups whose oxidation causes release of the dye moiety, and said compound comprising more than two leuco dye releasing moieties is dissolved in said oleophilic binder.

24. The photothermographic element according to claim 21 wherein said compound comprising more than one leuco dye releasing moiety comprises dyes in their reduced leuco forms which are oxidised in the redox process, thus generating a desired dye, and said dyes are simultaneously cleaved from the rest of the molecule.

25. A photothermographic element comprising a support bearing at least one photothermographic emulsion layer comprising:

(a) a photosensitive silver halide, (b) a non-photosensitive reducible silver source, (c) reducing agent for the non-photosensitive reducible silver source, and (d) an oleophilic polymeric binder, wherein said reducing agent comprises a compound comprising more than one leuco dye releasing moiety, and said reducing agent is dissolved in said oleophilic binder.

26. The photothermographic element according to claim 25 wherein said compound comprising more than one leuco dye releasing moiety comprises leuco dye moieties attached via oxidisable groups whose oxidation causes release of the leuco dye moiety, and said compound comprising more than one leuco dye releasing moiety is dissolved in said oleophilic binder.

27. The photothermographic element according to claim 25 wherein said compound comprising more than one leuco dye releasing moiety comprises dyes in their reduced leuco forms which are oxidised in the redox process, thus generating a desired dye, and said dyes are simultaneously cleaved from the rest of the molecule.

28. The photothermographic element according to claim 25 wherein said compound comprising more than one leuco dye releasing moiety has the general formula (I):

$$X\text{—}(\text{—}A\text{—}R^1\text{—}Y^1\text{—}D^1)_n \qquad (I)$$

wherein;

n is an integer of at least 2, each A is independently a member selected from the group consisting of a bond and divalent linking group, each $R^1$ independently represents a reducing group capable of being oxidised by a silver salt, each $Y^1$ independently represents a divalent linking group capable of being oxidatively cleaved from $R^1$ and/or $D^1$, each $D^1$ independently represents a dye moiety which forms a thermally diffusible dye on cleavage of a bond to $Y^1$, and X is a member selected from the group consisting of an atom and group to which each A is bonded.

29. The photothermographic element according to claim 25 wherein said compound comprising more than one leuco dye releasing moiety has the general formula (II);

$$X\text{—}(\text{—}A\text{—}Y^2\text{—}D^2)_n \qquad (II)$$

wherein;

X is independently a member selected from the group consisting of an atom and group to which each A is bonded, each A is independently a member selected from the group consisting of a bond and divalent linking group, n is an integer of at least 2, each $Y^2$ independently represents a divalent linking group capable of being oxidatively cleaved from $D^2$ and/or A, and each $\text{—}D^2$ independently represents a leuco dye moiety which forms a thermally diffusible dye on cleavage of a bond to $Y^2$.

* * * * *

UNITED STATES PATENT AND TRADEMARK OFFICE
CERTIFICATE OF CORRECTION

PATENT NO.: 5,663,042

DATED: Sept. 2, 1997

INVENTOR(S): Duncan McL. A. Grieve, et. al.

It is certified that error appears in the above-identified patent and that said Letters Patent is hereby corrected as shown below:

Column 27, line 45 the formula is missing a Y. It should read as follows:

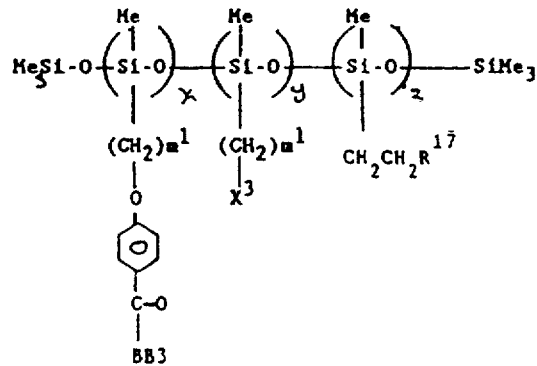

On Column 39, Compound K the formula is missing O. It should read as follows:

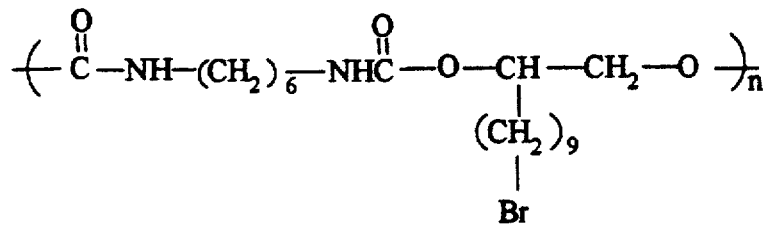

UNITED STATES PATENT AND TRADEMARK OFFICE
CERTIFICATE OF CORRECTION

PATENT NO. : 5,663,042
DATED : Sept. 2, 1997
INVENTOR(S) : Duncan McL. A. Grieve, et. al.

It is certified that error appears in the above-identified patent and that said Letters Patent is hereby corrected as shown below:

On Column 72, line 30 of Claim 19 it is missing L. It should read as follows:

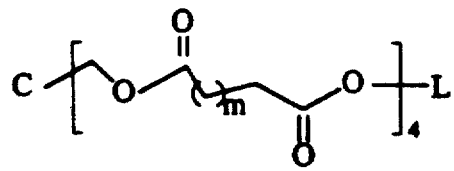

Signed and Sealed this

Twenty-seventh Day of January, 1998

Attest:

BRUCE LEHMAN

Attesting Officer

Commissioner of Patents and Trademarks